(12) United States Patent
Curran et al.

(10) Patent No.: US 6,750,199 B2
(45) Date of Patent: *Jun. 15, 2004

(54) ANTIMICROBIAL SULFONAMIDE DERIVATIVES OF LIPOPEPTIDE ANTIBIOTICS

(75) Inventors: William V. Curran, Pearl River, NY (US); Richard A. Leese, Suffern, NY (US); Howard Jarolmen, Fair Lawn, NJ (US); Donald B. Borders, Suffern, NY (US)

(73) Assignee: Micrologix Biotech Inc., Vancouver (CA)

( * ) Notice: Subject to any disclaimer, the term of this patent is extended or adjusted under 35 U.S.C. 154(b) by 76 days.

This patent is subject to a terminal disclaimer.

(21) Appl. No.: 09/904,756

(22) Filed: Jul. 13, 2001

(65) Prior Publication Data

US 2002/0028771 A1 Mar. 7, 2002

Related U.S. Application Data

(63) Continuation-in-part of application No. 09/760,328, filed on Jan. 12, 2001, now Pat. No. 6,511,962.
(60) Provisional application No. 60/219,059, filed on Jul. 17, 2000, and provisional application No. 60/220,950, filed on Jul. 26, 2000.

(51) Int. Cl.$^7$ ............................. A61K 38/12; C01K 7/56
(52) U.S. Cl. .......................................... 514/11; 530/317
(58) Field of Search .................. 435/68.1, 71.3; 514/9, 11; 530/317, 321

(56) References Cited

U.S. PATENT DOCUMENTS

| | | | |
|---|---|---|---|
| 3,639,582 A | 2/1972 | Umezawa et al. | 424/118 |
| 3,817,973 A | 6/1974 | Bouchaudon et al. | 530/319 |
| 4,331,594 A | 5/1982 | Hamill et al. | 260/112.5 R |
| 4,435,385 A | * 3/1984 | Bauer et al. | 514/11 |
| 4,495,348 A | 1/1985 | Kunishima et al. | 344/21 |
| 4,524,135 A | 6/1985 | Abbott et al. | 435/69 |
| 4,557,934 A | * 12/1985 | Cooper | 514/159 |
| 4,800,157 A | 1/1989 | Eaton et al. | 435/71 |
| 4,977,083 A | 12/1990 | Boeck | 435/71.3 |
| 4,994,270 A | 2/1991 | Boeck et al. | 514/9 |
| 5,028,590 A | 7/1991 | Fukuda et al. | 514/11 |
| 5,039,789 A | 8/1991 | Fukuda et al. | 530/317 |
| 5,057,313 A | * 10/1991 | Shih et al. | 424/1.53 |
| 5,629,288 A | 5/1997 | Lattrell et al. | 514/9 |
| 5,912,226 A | 6/1999 | Baker et al. | 514/9 |
| 6,146,872 A | 11/2000 | Ueda et al. | |
| 6,194,383 B1 | 2/2001 | Hammann et al. | 514/11 |
| 6,511,962 B1 | * 1/2003 | Borders et al. | 514/11 |

FOREIGN PATENT DOCUMENTS

| | | |
|---|---|---|
| WO | WO 98/00173 A2 | 1/1998 |
| WO | WO 99 21869 A1 | 5/1999 |

OTHER PUBLICATIONS

Bodanszky et al., "Structure of the Peptide Antibiotic Amphomycin", Journal of the Amer. Chem. Soc., 95:7, Apr. 4, 1973, pp. 2352–2357.
Debono et al., "Enzymatic and Chemical Modifications of Lipopeptide Antibiotic A21978C: The Synthesis and Evaluation of Daptomycin (LY146032)", The Journal of Antibiotics. vol. XLL No. 8, Aug. 1988, pp. 1093–1105.
Shay et al., "Aspartocin. I. Production, Isolation, and Characteristics", Antibiotics Annual 1959–1960. pp. 194–198.
Naganawa et al., "Laspartomycin, A New Anti–Staphylococcal Peptide", The Journal of Antibiotics, vol. 21:1, Jan. 1968, pp. 55–62.
Martin et al., "Isolation and Identification of D–α–Pipecolic Acid, α[L]β–Methylaspartic Acid and α, β–Diaminubutyric Acid from the Polypeptide Antibiotic Aspartocin", Communications to the Editor, Apr. 20, 1960, p. 2079.
Naganawa et al., A Novel Fatty Acid From Laspartomycin, The Journal of Antibiotics, vol. 23, No. 8, pp. 423–424, Aug. 1970.

* cited by examiner

Primary Examiner—Jeffrey Edwin Russel
(74) Attorney, Agent, or Firm—Seed IP Law Group PLLC

(57) ABSTRACT

The present invention provides antimicrobial sulfonamide derivatives of lipopeptide antibiotics, pharmaceutical compositions of antimicrobial sulfonamide derivatives, methods for making antimicrobial sulfonamide derivatives, methods for inhibiting microbial growth with antimicrobial sulfonamide derivatives and methods for treating or preventing microbial infections in a subject with antimicrobial sulfonamide derivatives. Antimicrobial sulfonamide derivatives are generally an amino core antibiotic that has been further modified with a lipophilic sulfonyl group.

45 Claims, No Drawings

ANTIMICROBIAL SULFONAMIDE DERIVATIVES OF LIPOPEPTIDE ANTIBIOTICS

This application is a continuation-in-part of U.S. patent application Ser. No. 09/760,328, filed Jan. 12, 2001, now U.S. Pat. No. 6,511,962 which claimed the benefit under 35 U.S.C. § 119(e) of U.S. Provisional Application No. 60/219,059, filed Jul. 17, 2000 and U.S. Provisional Application No. 60/220,950, filed Jul. 26, 2000. The above applications are incorporated herein by reference in their entirety.

FIELD OF THE INVENTION

The present invention relates to novel antibiotics and antimicrobial agents. More particularly, the present invention relates to antimicrobial sulfonamide derivatives of lipopeptide antibiotics.

BACKGROUND OF THE INVENTION

An important class of antibiotics that inhibit Gram-positive bacteria are the acidic lipopeptide antibiotics. Generally, acidic lipopeptide antibiotics consist of either a cyclic peptide core or a cyclic depsipeptide core acylated with a lipophilic fragment. The lipophilic fragment, typically an unsaturated fatty acid, may be of varying length. Frequently, the antibiotic activity of lipopeptide antibiotics is related to the length of the lipophilic fragment.

Examples of acidic lipopeptide antibiotics include, but are not limited to, laspartomycin (Umezawa et al., U.S. Pat. No. 3,639,582; Naganawa et al., 1968, *J. Antibiot.*, 21, 55; Naganawa et al., 1970, *J. Antibiot.*, 23, 423), zaomycin (Kuroya, 1960, *Antibiotics Ann.*, 194; Kuroya, Japanese Patent No. 8150), crystallomycin (Gauze et al., 1957, *Antibiotiki*, 2, 9), aspartocin (Shay et al., 1960, *Antibiotics Annual*, 194; Hausman et al., 1964, *Antimicrob. Ag. Chemother.*, 352; Hausman et al., 1969, *J. Antibiot.*, 22, 207; Martin et al., 1960, *J. Am. Chem. Soc.*, 2079), amphomycin (Bodanszky et. al., 1973, *J. Am. Chem. Soc.*, 95, 2352), glumamycin (Fujino et al., 1965, *Bull. Chem. Soc. Jap.*, 38, 515), brevistin (Shoji et al., 1976, *J. Antibiotics*, 29, 380), cerexin A (Shoji et al., 1976, *J. Antibiotics*, 29, 1268), cerexin B (Shoji et al., 1976, *J. Antibiotics*, 29, 1275), Antibiotic A-30912 (Hoehn et al., U.S. Pat. No. 5,039,789), Antibiotic A-1437 (Hammann et al., EP 0 629 636 B1; Lattrell et al., U.S. Pat. No. 5,629,288), Antibiotic A-54145 (Fukada et al., U.S. Pat. No. 5,039,789; Boeck et al., 1990, *J. Antibiotics*, 43, 587), Antibiotic A-21978C (Debono et al., 1988, *J. Antibiotics*, 41, 1093) and tsushimycin (Shoji et. al., 1968, *J. Antibiot.*, 21, 439). See also Berdy, "CRC Handbook of Antibiotic Compounds," Volume IV, Part 1, pages 313–327, CRC Press, Boca Raton, Fla., (1980); Korzybinski et al., "Antibiotics-Origin Nature and Properties," Vol. 1, Pergamon Press, pp. 397–401 and 404–408, New York, N.Y. (1967).

Despite the efficacy of lipopeptide antibiotics against Gram-positive bacteria, the medicinal chemistry of these antibiotics has remained largely unexplored. However, given the recent dramatic rise of antibiotic-resistant pathogens and infectious diseases, caused in part by frequent over use of antibiotics, the need for new antimicrobial agents is urgent (Cohen et al., 1992, *Science*, 257, 1050–1055). Methicillin resistant bacteria are a particular problem, since they are also frequently resistant to a wide variety of other antibiotics (Yoshida et al., U.S. Pat. No. 5,171,836). Gram-positive bacteria, such as Staphylococci, which cause persistent infections, are especially dangerous when methicillin resistant. Even more alarmingly, vancomycin-resistant strains of *Enterococcus faecium* have been observed (Moellering, 1990, *Clin. Microbiol. Rev.*, 3, 46). Strains resistant to vancomycin pose a serious health threat to society since vancomycin is the antibiotic of last resort for several harmful pathogens.

Thus, there is a need to explore the medicinal chemistry of lipopeptide antibiotics to develop novel antimicrobial agents. The discovery of new lipopeptide antibiotics will increase the repertoire of antibiotics available to combat pathogens resistant to currently available antibiotics.

SUMMARY OF THE INVENTION

In one aspect, the present invention provides antimicrobial sulfonamide derivatives of lipopeptide antibiotics. The sulfonamide derivatives generally comprise the peptidic portion of a lipopeptide antibiotic ("core antibiotic" or "core cyclic peptide") and a lipophilic moiety. The lipophilic moiety is linked to the amino core antibiotic or amino core cyclic peptide, either directly or by way of an optional intervening linker. The lipophilic moiety and core antibiotic or core cyclic peptide are connected by a linkage containing at least one sulfonamide group. When an optional linker is used, the sulfonamide linkage may be between (i) the linker and the core antibiotic or core cyclic peptide; (ii) the lipophilic moiety and the linker; or both (i) and (ii) above.

The core antibiotic is the molecule obtained by enzymatic removal of the lipophilic moiety of a lipopeptide antibiotic, typically with a deacylase such as that produced by *Actinoplanes utahensis* (NRRL 12052). Lipopeptide antibiotics which may be used to provide a core antibiotic, include by way of example and not limitation, laspartomycin, zaomycin, crystallomycin, aspartocin, amphomycin, glumamycin, brevistin, cerexin A, cerexin B, Antibiotic A-30912, Antibiotic A-1437, Antibiotic A-54145, Antibiotic A-21978C and tsushimycin. Those of skill in the art will recognize that for some of these lipopeptide antibiotics, removal of the lipophilic portion via enzymatic deacylation yields a cyclic peptide or depsipeptide having one or more additional amino acids attached thereto. In some instances these additional exocyclic amino acids may be necessary for activity and should not be removed by further enzymatic degradation. When enzymatic deacylation yields a cyclic peptide or depsipeptide having additional exocyclic amino acids attached thereto, the "core antibiotic" includes the exocyclic amino acids. The core cyclic peptide is a cyclic peptide or depsipeptide with no exocyclic amino acids. In some situations the core cyclic peptide and the core antibiotic may refer to the same molecule (e.g., Antibiotic A-30912).

The lipophilic moiety may be a saturated or unsaturated fatty acid. The fatty acid may be branched or a straight-chain. Unsaturated fatty acids may be mono, di, tri, or polyunsaturated. The lipophilic moiety may also be substituted with heteroatoms, aryl groups, heteroaryl groups and the like and may also be mono, di, tri, or polyunsaturated. In some situations the lipophilic moiety may consist of a aryl group, arylaryl group, biaryl group, heteroaryl group and the like.

The optional linker may comprise virtually any molecule capable of linking the lipophilic moiety to the core antibiotic. Linkers suitable for use are typically at least bi-functional, having one functional group capable of forming a covalent linkage with an exocyclic amine of the core antibiotic and another functional group capable of forming a covalent linkage with a complementary functional group on a precursor of the lipophilic moiety. At least one of the linkages formed and optionally both of the linkages formed are a sulfonamide linkage.

A wide variety of linkers suitable for spacing the lipophilic group from the core antibiotic or core cyclic peptide of a lipopeptide antibiotic are known in the art and include by way of example and not limitation, linkers that contain alkyl, heteroalkyl, acyclic heteroatomic bridges, aryl, arylaryl, arylalkyl, heteroaryl, heteroaryl-heteroaryl, substituted heteroaryl-heteroaryl, heteroarylalkyl, heteroaryl-heteroalkyl and the like. Linkers may include single, double, triple or aromatic carbon-carbon bonds, nitrogen-nitrogen bonds, carbon-nitrogen, carbon-oxygen bonds and/or carbon-sulfur bonds and include functionalities such as carbonyls, ethers, thioethers, carboxamides, sulfonamides, ureas, urethanes, hydrazines, etc.

The linker may be flexible or rigid. Rigid linkers include, for example, polyunsaturated alkyl, aryl, biaryl, heteroaryl, etc. Flexible linkers include, for example, a flexible peptide such as Gly-Gly-Gly or a flexible saturated alkanyl or heteroalkanyl. The linker may be hydrophilic or hydrophobic. Hydrophilic linkers include, for example, polyalcohols or polyethers such as polyalkyleneglycols. Hydrophobic linkers may be, for example, alkyls or aryls.

In another aspect, the present invention provides methods for making antimicrobial sulfonamide derivatives. Generally the methods involve assembling three fragments of the sulfonamide derivatives: the amino core antibiotic or amino core cyclic peptide, the optional linker and the lipophilic moiety in any convenient order. The only requirement is that the precursor of the lipophilic moiety and/or linker bear appropriate functional groups such that the assembly of the fragments result in the formation of at least one sulfonamide linkage. For example, a lipophilic sulfonyl derivative may be covalently attached to a amino core antibiotic or amino core cyclic peptide. As another example, a linker may be first covalently attached to an amino core antibiotic or amino core cyclic peptide and then a lipophilic sulfonyl attached therefore. As still another example, a lipophilic sulfonyl derivative may be covalently attached to a linker and the resultant lipophilic linker covalently attached to a amino core antibiotic or amino core cyclic peptide.

In still another aspect, the present invention provides pharmaceutical compositions comprising antimicrobial sulfonamide derivatives of the invention. The pharmaceutical compositions generally comprise one or more antimicrobial sulfonamide derivatives of the invention, (or salts thereof) and an adjuvant, carrier, excipient or diluent. The pharmaceutical composition may be formulated for environmental use, such as for application on plants, for vetinary use or for pharmaceutical use. The choice of adjuvant, carrier, excipient or diluents will depend on the particular application.

In yet another aspect, the present invention provides methods of inhibiting the growth of microbes such as Gram-positive bacteria. The method generally involves contacting a microbe with one or more antimicrobial sulfonamide derivatives of the invention or a salt thereof or a pharmaceutical composition thereof in an amount effective to inhibit the growth of the microbe. The method may be practical to achieve a bacteriostatic effect, where the growth of the microbe is inhibited, or to achieve a bactericidal effect, where the microbe is killed.

In a final aspect, the present invention provides methods for treating and/or preventing microbial infections in a subject such as a human, a plant or an animal. The methods generally involve administering to a subject one or more of the antimicrobial sulfonamide derivatives, salts or compositions of the invention in an amount effective to treat or prevent a microbial infection in the human, animal or plant. The antimicrobial sulfonamide derivatives, salts or compositions may be administered systemically or applied topically, depending on the nature of the microbial infection.

DETAILED DESCRIPTION OF THE INVENTION

4.1 Definitions

As used herein, the following terms shall have the following meanings:

"Core cyclic peptide" refers to the desamino portion cyclic peptide or cyclic depsipeptide portion of a lipopeptide antibiotic that remains after the lipophilic portion of a lipopeptide antibiotic, including any exocyclic amino acids, has been removed. As illustrative examples, the core cyclic peptides derived from the lipopeptide antibiotics laspartomycin (2), aspartocin (4), antibiotic A-21978C (6), antibiotic A-54145 (8), antibiotic A-30912A (10), antibiotic A-30912B (12), antibiotic A-30912D (14) and antibiotic A-30912H (16) are depicted below:

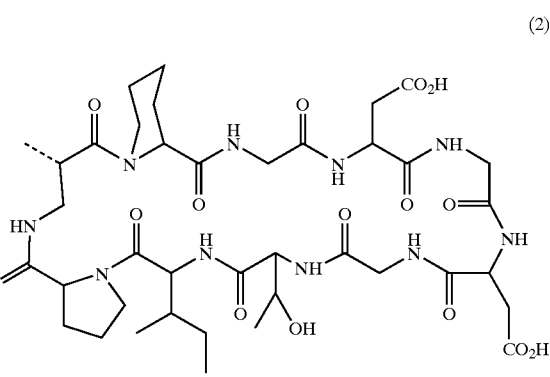

(2)

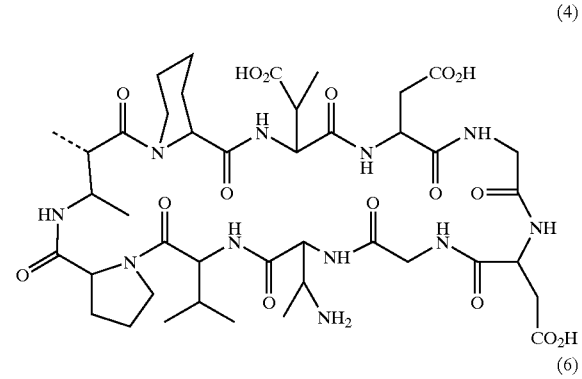

(4)

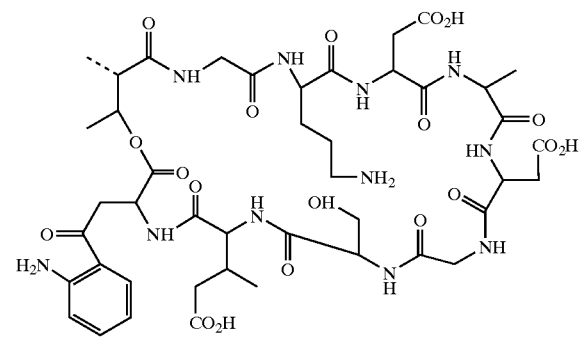

(6)

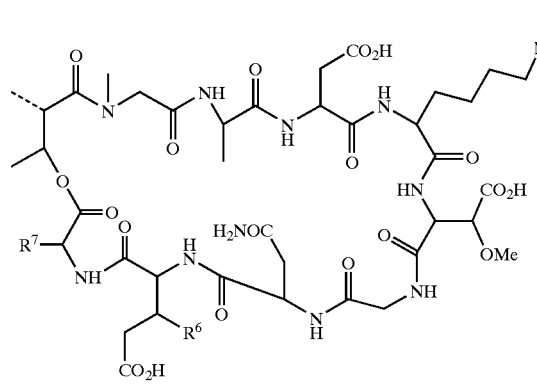

(8)

R⁷ is isopropyl or isobutyl     R⁶ is hydrogen or methyl

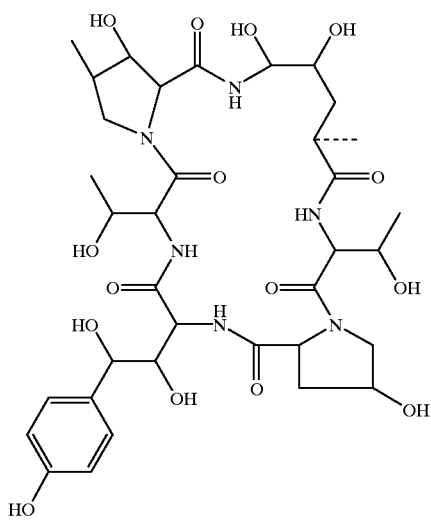

(10)

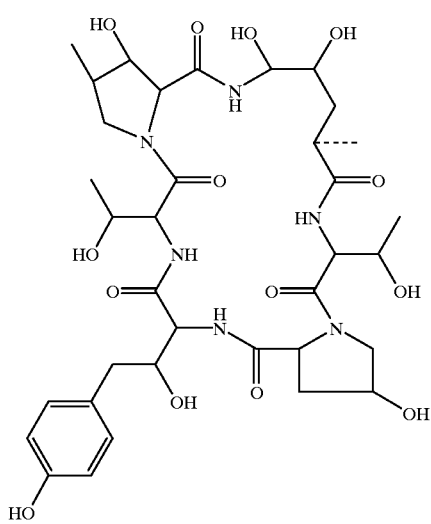

(12)

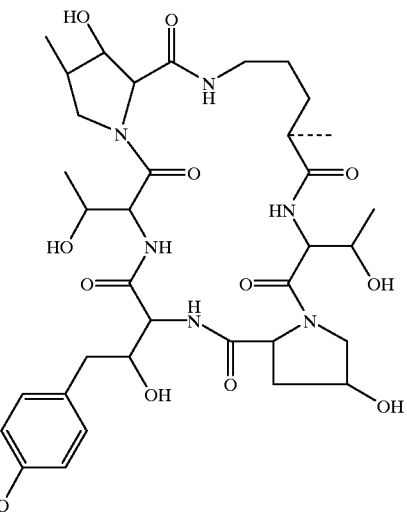

(14)

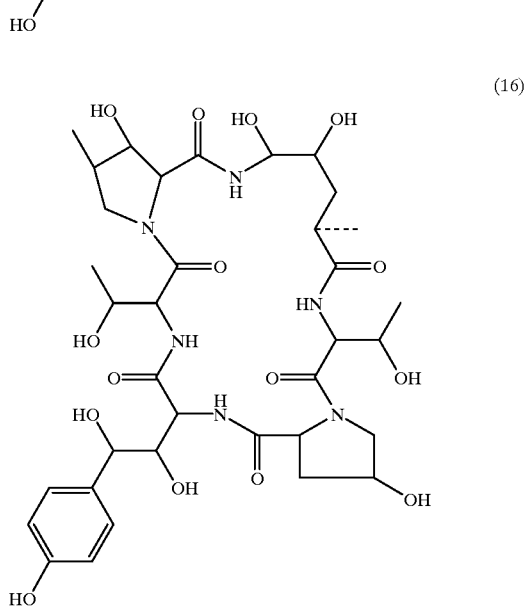

(16)

As used herein, "core cyclic peptide" includes both conventional cyclic peptides, such as the cyclic peptides derived from aspartocin (4) as well as cyclic depsipeptides such as the cyclic depsipeptide derived from Antibiotic A-21978C (6) and Antibiotic A-54145 (8). The dashed lines in structures 2, 4, 6, 8, 10, 12, 14 and 16 indicate points of attachment of the amido lipophilic portion of the parent lipopeptide antibiotic or, for those lipopeptide antibiotics in which the amino lipophilic portion is linked to the core peptide via intervening exocyclic amino acid residues, the dashed lines indicate the point of attachment of the amino group of exocyclic amino acid residues.

"Amino core cyclic peptide" refers to a core cyclic peptide as defined above where a primary amino group is attached to the dashed lines in structures 2, 4, 6, 8, 10, 12, 14 and 16.

"Core antibiotic" refers to the des-amino peptide portion of the lipopeptide antibiotic that remains after cleavage of the lipophilic fragment. As illustrative examples, the core antibiotics derived from the lipopeptide antibiotics laspartomycin 18, aspartocin 20, antibiotic A-21978C 22, antibiotic A-54145 24 and Antibiotic A-30912A 26 are depicted below:

(18)
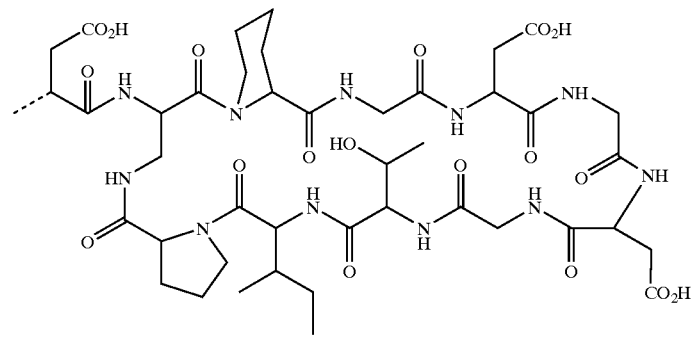
(20)
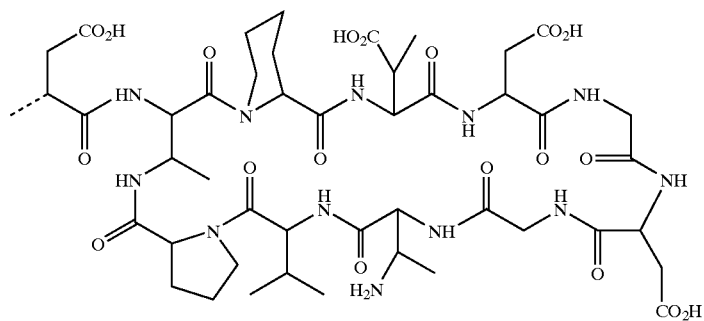
(22)
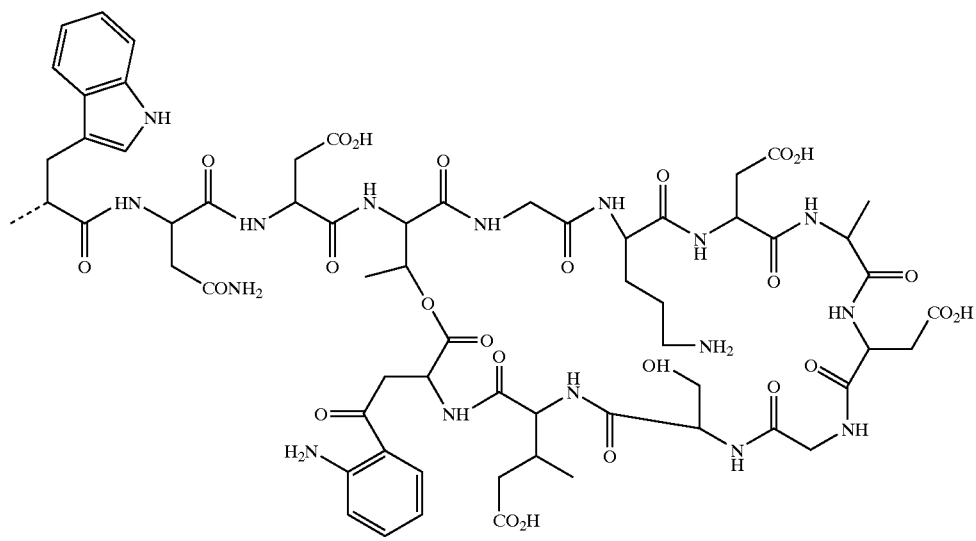

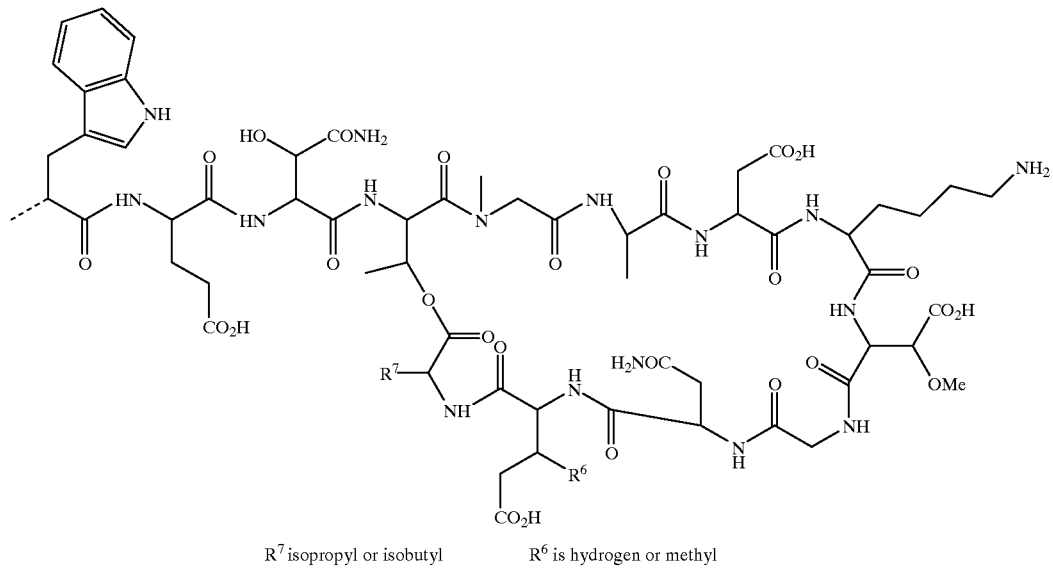

(24)

R⁷ isopropyl or isobutyl     R⁶ is hydrogen or methyl

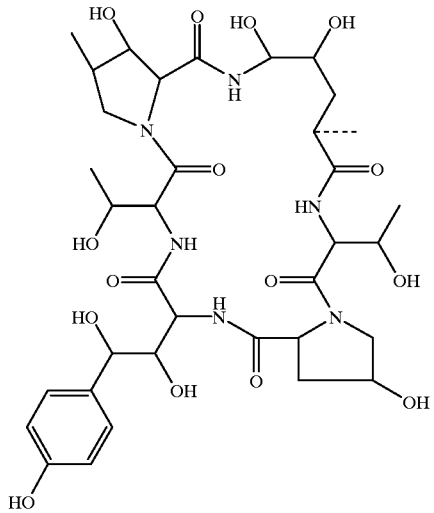

(26)

In structures 18, 20, 22, 24 and 26, the dashed lines indicate the point of attachment of the amine group that joins the lipophilic moiety and the core antibiotic in the naturally occurring antibiotic. The structures of core antibiotics derived from Antibiotic A-30912B, Antibiotic A-30912D and Antibiotic A-30912H will be apparent to those of skill in the art.

"Amino core antibiotic" refers to a core antibiotic as defined above where a primary amino group is attached to the dashed lines in structures 18, 20, 22, 24 and 26.

"FMOC derivative of the core antibiotic of aspartocin" refers to the following compound:

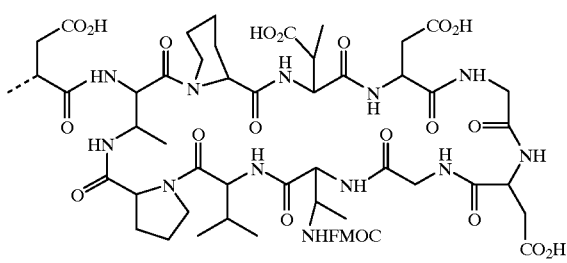

27

"t-butyl derivative of the core antibiotic of laspartomycin" refers to the following compound:

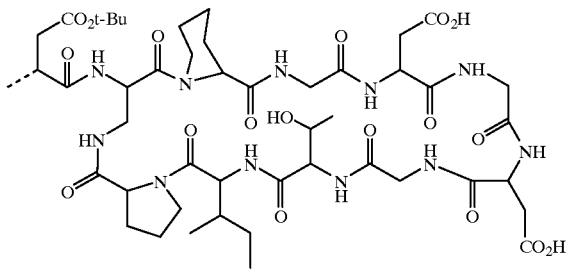

28

As will be recognized by those of skill in the art, in some circumstances, the core antibiotic and core cyclic peptide of a lipopeptide antibiotic may be the same (see, e.g., the core cyclic peptide 10 and core antibiotic 26 derived from antibiotic A-30912A). Also, the core antibiotic and the core cyclic peptide may be different (see, e.g., the core cyclic peptide 2 and core antibiotic 18 derived from laspartomycin). Also, in some instances, the amino core antibiotic, which may include an exocyclic amino acid or peptide, may be further deacylated further to yield the corresponding amino core cyclic peptide. For example, deacylation of laspartomycin with a deacylase produced by fermentation of *Actinoplanes utahensis* (NRRL 12052) yields both the amino core cyclic peptide of laspartomycin and the amino core antibiotic of laspartomycin.

"A-30912" refers to all naturally occurring A-30912 compounds. When reference to a specific A-30912 compound or nucleus is intended, then a specific designation such as A-30912 A, A-30912 B, A-30912 C, etc. is used.

"A-21978C" refers to all naturally occurring A-21978C compounds and is intended to include anhydro and isomeric forms (Baker et al., U.S. Pat. No. 5,912,225). When reference to a specific A-21978C compound or nucleus is intended, then a specific designation such as anhydro- and isomer, etc. is used.

"A-54145" refers to all naturally occurring A-54145 compounds. When reference to a specific A-54145 compound or nucleus is intended, then a specific designation is used.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used.

"Alkanyl" refers to a saturated branched, straight-chain or cyclic alkyl group. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Arylaryl" refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, ($C_5$–$C_{14}$) arylaryl is an arylaryl group in which each aromatic ring comprises from 5 to 14 carbons, e.g., biphenyl, triphenyl, binaphthyl, phenylnaphthyl, etc. Preferably, each parent aromatic ring system of an arylaryl group is independently a ($C_5$–$C_{14}$) aromatic, more preferably a ($C_5$–$C_{10}$) aromatic. Also preferred are arylaryl groups in which all of the parent aromatic ring systems are identical, e.g., biphenyl, triphenyl, binaphthyl, trinaphthyl, etc.

"Biaryl" refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are ($C_5$–$C_{14}$) aromatic rings, more preferably ($C_5$–$C_{10}$) aromatic rings. A particularly preferred biaryl group is biphenyl.

"Arylalkyl" refers to an acyclic alkyl group in which one of the hydrogen atoms bonded to a carbon atom, typically a terminal or sp³ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is ($C_6$–$C_{20}$) arylalkyl, e.g., the alkanyl, alkenyl or alkynyl moiety of the arylalkyl group is ($C_1$–$C_6$) and the aryl moiety is ($C_5$–$C_{14}$). In particularly preferred embodiments the arylalkyl group is ($C_6$–$C_{13}$), e.g., the alkanyl, alkenyl or alkynyl moiety of the arylalkyl group is ($C_1$–$C_3$) and the aryl moiety is ($C_5$–$C_{10}$).

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroarylalkyl" refers to an acyclic alkyl group in which one of the hydrogen atoms bonded to a carbon atom, typically a terminal or Sp³ carbon atom, is replaced with a heteroaryl group. Where specific alkyl moieties are intended, the nomenclature heteroarylalkanyl, heteroarylakenyl and/or heterorylalkynyl is used.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent Heteroaromatic Ring System" refers to a parent aromatic ring system in which one or more carbon atoms (and any associated hydrogen atoms) are each independently replaced with the same or different heteroatom. Typical heteratoms to replace the carbon atoms include, but are not limited to, N, P, O, S, Si, etc. (Including and associated hydrogen or other atoms). Specifically included within the definition of "parent heteroaromatic ring systems" are fused ring systems in which one or more of the rings are aromatic and one or more of the rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like.

Reference will now be made in detail to preferred embodiments of the invention. While the invention will be described in conjunction with preferred embodiments, it should be understood that it is not intended to limit the invention to these preferred embodiments. To the contrary, it is intended to cover alternatives, modifications, and equivalents as may be included within the spirit and scope of the invention as defined by the appended claims.

4.2 The Invention

The present invention provides antimicrobial sulfonamide derivatives, pharmaceutical compositions comprising antimicrobial sulfonamide derivatives, methods for making antimicrobial sulfonamide derivatives, methods for inhibiting microbial growth with antimicrobial sulfonamide derivatives and methods for treating or preventing microbial infections in a subject with antimicrobial sulfonamide derivatives.

Examples of acidic lipopeptide antibiotics that may be converted to antimicrobial sulfonamide derivatives include, but are not limited to, laspartomycin (Umezawa et al., U.S. Pat. No. 3,639,582; Naganawa et al., 1968, *J. Antibiot.*, 21, 55; Naganawa et al., 1970, *J. Antibiot.*, 23, 423), zaomycin (Kuroya, 1960, *Antibiotics Ann.*, 194; Kuroya, Japanese Patent No. 8150), crystallomycin (Gauze et al., 1957, *Antibiotiki*, 2, 9), aspartocin (Shay et al., 1960, *Antibiotics Annual*, 194; Hausman et al., 1964, *Antimicrob. Ag. Chemother.*, 352; Hausman et al., 1969, *J. Antibiot.*, 22, 207; Martin et al., 1960, *J. Am. Chem. Soc.*, 2079), amphomycin (Bodanszky et. al., 1973, *J. Am. Chem. Soc.*, 95, 2352), glumamycin (Fujino et al., 1965, *Bull. Chem. Soc. Jap.*, 38, 515), brevistin (Shoji et al., 1976, *J. Antibiotics*, 29, 380), cerexin A (Shoji et al., 1976, *J. Antibiotics*, 29, 1268), cerexin B (Shoji et al., 1976, *J. Antibiotics*, 29, 1275), daptomycin (Debono et. al., 1988, *J. Antibiotics*, 41, 1093), Antibiotic A-30912 (Hoehn et al., U.S. Pat. No. 5,039,789), Antibiotic A-1437 (Hammann et al., EP 0 629 636 B1;

Lattrell et al., U.S. Pat. No. 5,629,288), Antibiotic A-54145 (Fukada et al., U.S. Pat. No. 5,039,789; Boeck et al., 1990, *J. Antibiotics*, 43, 587), Antibiotic A-21978C (Debono et al., 1988, *J. Antibiotics*, 41, 1093) and tsushimycin (Shoji et. al., 1968, *J. Antibiot.*, 21, 439).

4.2.1 Antimicrobial Sulfonamide Derivatives

Antimicrobial sulfonamide derivatives of the present invention offer some significant advantages over traditional antibiotics. Antimicrobial sulfonamide derivatives are generally active against many gram positive bacteria. More importantly, antimicrobial sulfonamide derivatives of the present invention may be effective against methicillin resistant bacteria and/or strains resistant to vancomycin. Thus, antimicrobial sulfonamide derivatives may inhibit or prevent growth of a number of microbes generally resistant to known antibiotics. Further, antimicrobial sulfonamide derivatives may offer greater resistance to microbial proteases than the corresponding antimicrobial amide derivatives. Accordingly, use of antimicrobial sulfonamide derivatives may be less likely to lead to the formation of antibiotic-resistant pathogens than conventional antimicrobial agents.

Those of skill in the art will appreciate that many of the compounds and compound species described herein may exhibit the phenomena of tautomerism, conformational isomerism, geometric isomerism and/or stereoisomerism. As the formula drawings within the specification can represent only one of the possible tautomeric, conformational isomeric, enantiomeric or geometric isomeric forms, it should be understood that the invention encompasses any tautomeric, conformational isomeric, enantiomeric and/or geometric isomeric forms of the compounds having one or more of the utilities described herein, as well as mixtures of these various different forms.

The present invention provides antimicrobial sulfonamide derivatives according to structural formula (I):

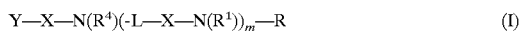

$$Y\text{—}X\text{—}N(R^4)(\text{-}L\text{—}X\text{—}N(R^1))_m\text{—}R \qquad (I)$$

wherein:
Y is a lipophilic moiety;
each X is independently selected from the group consisting of —CO—, —SO$_2$—, —CS—, —PO—, —OP(O)—, —OC(O)—, —NHCO— and —N(R$^1$)CO— with the proviso that at least one X is —SO$_2$—;
m is 0 or 1;
L is a linker;
N is nitrogen;
R$^1$ and R$^4$ are each independently selected from the group consisting of hydrogen, (C$_1$–C$_{25}$) alkyl optionally substituted with one or more of the same or different R$^2$ groups, (C$_1$–C$_{25}$) heteroalkyl optionally substituted with one or more of the same or different R$^2$ groups, (C$_5$–C$_{30}$) aryl optionally substituted with one or more of the same or different R$^2$ groups, (C$_5$–C$_{30}$) arylaryl optionally substituted with one or more of the same or different R$^2$ groups, (C$_5$–C$_{30}$) biaryl optionally substituted with one or more of the same or different R$^2$ groups, five to thirty membered heteroaryl optionally substituted with one or more of the same or different R$^2$ groups, (C$_6$–C$_{30}$) arylalkyl optionally substituted with one or more of the same or different R$^2$ groups and six to thirty membered heteroarylalkyl optionally substituted with one or more of the same or different R$^2$ groups;
each R$^2$ is independently selected from the group consisting of —OR$^3$, —SR$^3$, —NR$^3$R$^3$, —CN, —NO$_2$, —N$_3$, —C(O)OR$^3$, —C(O)NR$^3$R$^3$, —C(S)NR$^3$R$^3$, —C(NR$^3$) NR$^3$R$^3$, —CHO, —R$^3$CO, —SO$_2$R$^3$, —SOR$^3$, —PO(OR$^3$)$_2$, —PO(OR$^3$), —CO$_2$H, —SO$_3$H, —PO$_3$H, halogen and trihalomethyl;
each R$^3$ is independently selected from the group consisting of hydrogen, (C$_1$–C$_6$) alkyl, (C$_5$–C$_{10}$) aryl, five to sixteen membered heteroaryl, (C$_6$–C$_{16}$) arylalkyl and six to sixteen membered heteroarylalkyl; and
R is a core cyclic peptide or a core antibiotic of a lipopeptide antibiotic.

When m is 1 the antimicrobial sulfonamide derivatives of the invention are represented by structural formula (II):

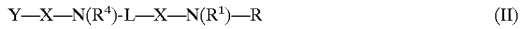

$$Y\text{—}X\text{—}N(R^4)\text{-}L\text{—}X\text{—}N(R^1)\text{—}R \qquad (II)$$

Here, the nitrogen atom covalently bonded to R$^1$ is directly attached to the core cyclic peptide or core antibiotic of a lipopeptide antibiotic (see section 4.1). The nitrogen atom covalently bonded to R$^4$ is covalently bonded to both the sulfonyl group and the linker L.

In a preferred embodiment, R$^1$ and R$^4$ are independently selected from the group consisting of hydrogen, (C$_1$–C$_{10}$) alkyl optionally substituted with one or more of the same or different R$^2$ groups, (C$_1$–C$_{10}$) heteroalkyl optionally substituted with one or more of the same or different R$^2$ groups, (C$_5$–C$_{15}$) aryl optionally substituted with one or more of the same or different R$^2$ groups, (C$_5$–C$_{15}$) biaryl optionally substituted with one or more of the same or different R$^2$ groups, five to sixteen membered heteroaryl optionally substituted with one or more of the same or different R$^2$ groups, (C$_6$–C$_{16}$) arylalkyl optionally substituted with one or more of the same or different R$^2$ groups and six to sixteen membered heteroarylalkyl optionally substituted with one or more of the same or different R$^2$ groups where R$^2$ is a substituent as defined above in Formula (I).

Preferably, R$^1$ and R$^4$ are independently selected from the group consisting of hydrogen, (C$_1$–C$_6$) alkanyl optionally substituted with one or more of the same or different R$^2$ groups, (C$_3$–C$_7$) alkenyl optionally substituted with one or more of the same or different R$^2$ groups, C$_6$ aryl optionally substituted with one or more of the same or different R$^2$ groups, C$_{12}$ biaryl optionally substituted with one or more of the same or different R$^2$ groups, five to sixteen membered heteroaryl optionally substituted with one or more of the same or different R$^2$ groups, (C$_6$–C$_{10}$) arylalkyl optionally substituted with one or more of the same or different R$^2$ groups and (C$_6$–C$_{10}$) heteroarylalkyl optionally substituted with one or more of the same or different R$^2$ groups, where R$^2$ is a substituent as defined above in Formula (I). More preferably, R$^1$ and R$^4$ are independently selected from the group consisting of hydrogen, methyl, allyl, homoallyl, phenyl optionally substituted with one or more of the same or different R$^2$ groups and benzyl optionally substituted with one or more of the same or different R$^2$ groups, where R$^2$ is a substituent as defined above in Formula (I). Most preferably, R$^1$ and R$^4$ are hydrogen.

When the antimicrobial sulfonamide derivative is described by structural formula (II) (i.e., Y—X—N(R$^4$)-L—X—N(R$^1$)—R), the moiety X may be any kind of chemical functionality that can form a covalent bond with nitrogen with the proviso that at least one X is —SO$_2$—. Preferably, X is —CO—, —SO$_2$—, —CS—, —PO—, —OPO—, —OC (O)—, —NHCO— or —NR$^5$CO— where R$^7$ is selected from the group consisting of hydrogen, (C$_1$–C$_6$) alkyl, (C$_5$–C$_{10}$) aryl, five to sixteen membered heteroaryl, (C$_6$–C$_{16}$) arylalkyl and six to sixteen membered heteroarylalkyl. More preferably, X is —CO— or —SO$_2$.

Connected to X—N(R$^1$) in the antimicrobial sulfonamide derivative described by Formula (II) (i.e., Y—XN(R$^4$)-L—X—N(R$^1$)—R) is a linker L and a nitrogen group (i.e., N(R$^4$)). The nature of linker L may vary extensively. Thus, for example, L may be hydrophilic or hydrophobic, long or short, rigid, semirigid or flexible etc.

A wide variety of linkers L comprised of stable bonds suitable for spacing the lipophilic group Y from the core cyclic peptide or core antibiotic of a lipopeptide antibiotic are known in the art, and include by way of example and not limitation, linkers such as alkyl, heteroalkyl, acyclic heteroatomic bridges, aryl, arylaryl, arylalkyl, heteroaryl, heteroaryl-heteroaryl, substituted heteroaryl-heteroaryl, heteroarylalkyl, heteroaryl-heteroalkyl and the like. Thus, linker L may include single, double, triple or aromatic carbon-carbon bonds, nitrogen-nitrogen bonds, carbon-nitrogen, carbon-oxygen bonds and/or carbon-sulfur bonds, and may therefore include functionalities such as carbonyls, ethers, thioethers, carboxamides, sulfonamides, ureas, urethanes, hydrazines, etc.

Choosing a suitable linker is within the capabilities of those of skill in the art. For example, where a rigid linker is desired, L may be a rigid polyunsaturated alkyl or an aryl, biaryl, heteroaryl, etc. Where a flexible linker is desired, L may be a flexible peptide such as Gly-Gly-Gly or a flexible saturated alkanyl or heteroalkanyl. Hydrophilic linkers may be, for example, polyalcohols or polyethers such as polyalkyleneglycols. Hydrophobic linkers may be, for example, alkyls or aryls.

Some embodiments of $N(R^4)$-L include, for example, compounds where L is —$(CH_2)_k$—, k is an integer between 1 and 8 and the corresponding analogues where any suitable hydrogen is independently substituted with one or more of the same or different $R^2$ groups, where $R^2$ is defined as above in Formula (I). Other embodiments of $N(R^4)$-L include any amino acid or peptide, which may be for example, a D or L α-amino acid, a β-amino acid, a γ-amino acid, a dipeptide, a tripeptide or a tetrapeptide comprised of any combination of amino acids preferably, α-amino acids). The polarity of the peptide bond in these peptides may be either C→N or N→C.

In a preferred embodiment, when m is 1, L is selected from the group consisting of:

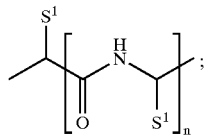
(L1)

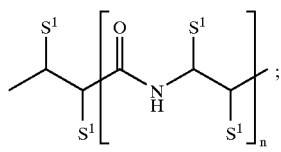
(L2)

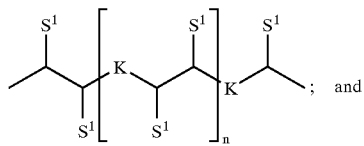
(L3)

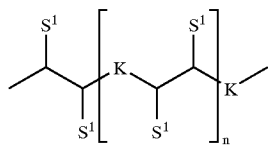
(L4)

or a pharmaceutically acceptable salt or hydrate thereof, wherein:

n is 0, 1, 2 or 3;

each $S^1$ is independently selected from the group consisting of hydrogen, $(C_1-C_{10})$ alkyl optionally substituted with one or more of the same or different $R^5$ groups, $(C_1-C_{10})$ heteroalkyl optionally substituted with one or more of the same or different $R^5$ groups, $(C_5-C_{10})$ aryl optionally substituted with one or more of the same or different $R^5$ groups, $(C_5-C_{15})$ arylaryl optionally substituted with one or more of the same or different $R^5$ groups, $(C_5-C_{15})$ biaryl optionally substituted with one or more of the same or different $R^5$ groups, five to ten membered heteroaryl optionally substituted with one or more of the same or different $R^5$ groups, $(C_6-C_{16})$ arylalkyl optionally substituted with one or more of the same or different $R^5$ groups and six to sixteen membered heteroarylalkyl optionally substituted with one or more of the same or different $R^5$ groups;

each $R^5$ is independently selected from the group consisting of —$OR^6$, —$SR^6$, —$NR^6R^6$, —$CN$, —$NO_2$, —$N_3$, —$C(O)OR^6$, —$C(O)NR^6R^6$, —$C(S)NR^6R^6$, —$C(NR^6)NR^6R^6$, —$CHO$, —$R^6CO$, —$SO_2R^6$, —$SOR^6$, —$PO(OR^6)_2$, —$PO(OR^6)$, —$CO_2$, —$SO_3H$, —$PO_3H$, halogen and trihalomethyl;

each $R^6$ is independently selected from the group consisting of hydrogen, $(C_1-C_6)$ alkyl, $(C_5-C_{10})$ aryl, five to ten membered heteroaryl, $(C_6-C_{16})$ arylalkyl and six to sixteen membered heteroarylalkyl; and each K is independently selected from the group consisting of oxygen, nitrogen and sulfur.

In a preferred embodiment, each $S^1$ is independently a side chain of a genetically encoded a amino acid. Exemplary preferred embodiments, where K is oxygen or nitrogen and $S^1$ is hydrogen, include the following compounds where R, $R^1$, $R^4$ and Y are as previously defined:

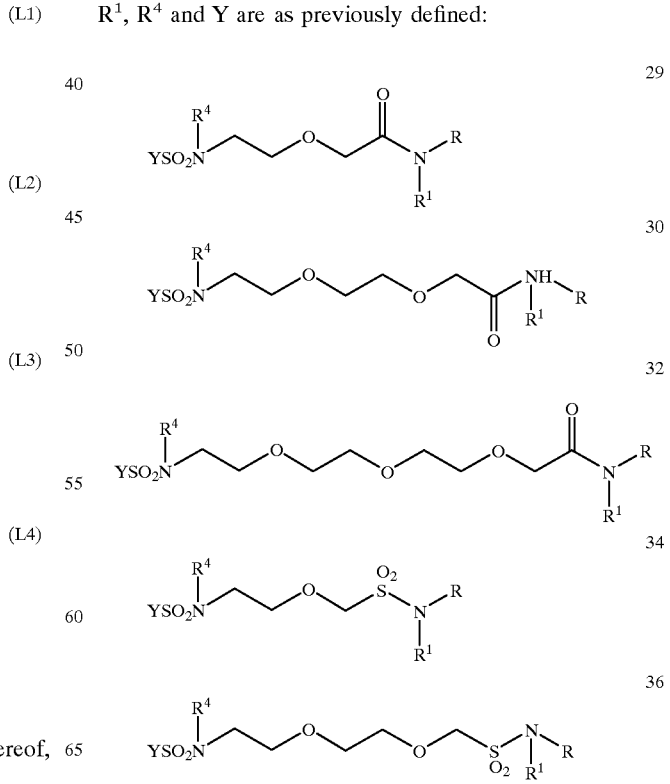

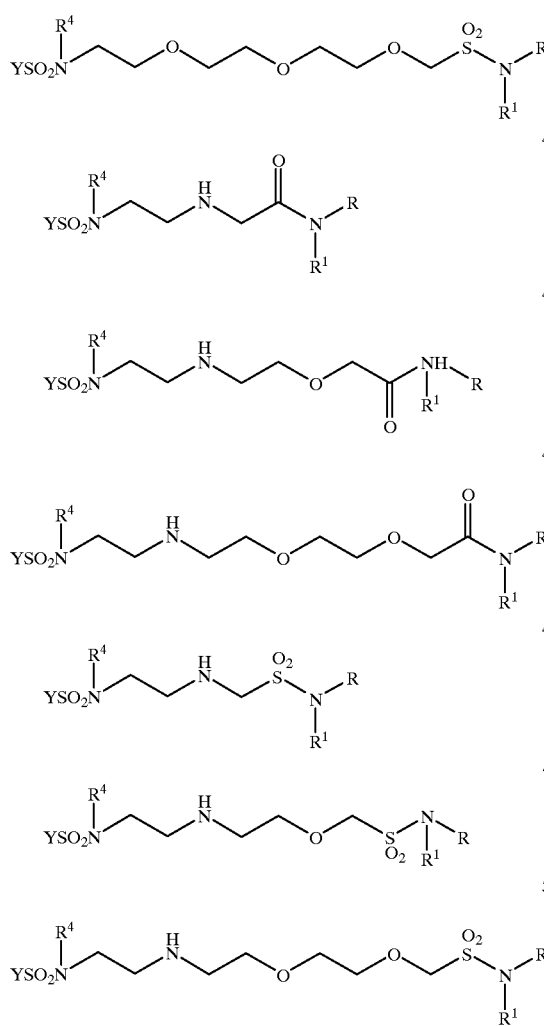

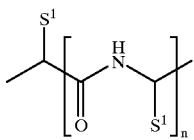

where n is as previously defined. Preferably, each $S^1$ is independently the side chain of a genetically encoded α amino acid.

In a preferred embodiment, n is 0 and $S^1$ is —$CH_2$—$CO_2H$, —$CH_2$—$CH_2$—$CO_2H$, —C(OH)H—$CONH_2$, —$CH_2$—$CONH_2$ or —$CH_2$—$CH_2$—$CONH_2$. In another preferred embodiment, n is 0 and $S^1$ is —$CH_2$—indol-2-yl or —$CH_2$-phenyl.

In one embodiment, n is 0, $R^4$ is hydrogen and R is the core antibiotic of aspartocin or the FMOC derivative of the core antibiotic of aspartocin. In one preferred embodiment, $S^1$ is H and $Y^2$ is decan-yl. In another preferred embodiment, $S^1$ is —$CH_2$-phenyl and $Y^2$ is hexadecan-yl.

In another embodiment, n is 0, $R^4$ is hydrogen and R is the core antibiotic of laspartomycin. In one preferred embodiment, $S^1$ is —$CH_2$-indol-2-yl and $Y^2$ is hexadecan-yl. In another preferred embodiment, $S^1$ is —$CH_2$-phenyl and $Y^2$ is hexadecan-yl. In another preferred embodiment, $S^1$ is —$CH_2$-phenyl and $Y^2$ is decan-yl.

In another embodiment, n is 0, $R^4$ is hydrogen and R is the core cyclic peptide of laspartomycin. In one preferred embodiment, $S^1$ is —$CH_2$-indol-2-yl and $Y^2$ is hexadecan-yl.

In still another preferred embodiment, L is:

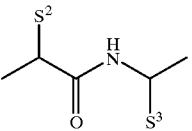

Preferably, $S^2$ and $S^2$ are the side chain of a genetically encoded α amino acid. In one embodiment, n is 1, $S^2$ is hydrogen, —$CH_2$-indol-2-yl, —$CH_2$—$CONH_2$ or —$CH_2$—$CH_2$—$CONH_2$ and $S^3$ is —$CH_2$—$CO_2H$ or —$CH_2$—$CH_2$—$CO_2H$. In another embodiment, n is 1, $S^2$ is —$CH_2$—$CO_2H$ or —$CH_2$—$CH_2$—$CO_2H$ and $S^3$ is —C(OH)H—$CONH_2$.

In still another preferred embodiment L is:

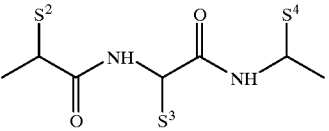

Preferably, $S^2$, $S^3$ and $S^4$ are the side chain of a genetically encoded a amino acid. In one embodiment, n is 2, $S^2$ is —$CH_2$-indol-2-yl, $S^3$ is —$CH_2$—$CONH_2$ or —$CH_2$—$CH_2$—$CONH_2$ and $S^4$ is —$CH_2$—$CO_2H$ or —$CH_2$—$CH_2$—$CO_2H$. In another embodiment, n is 2, $S^2$ is —$CH_2$-indol-2-yl, $S^3$ is —$CH_2$—$CO_2H$ or $CH_2$—$CH_2$—$CO_2H$— and $S^4$ is —$CH_2$—$CONH_2$, —$CH_2$—$CH_2$—$CONH_2$ or —C(OH)H—$CONH_2$.

Preferably, R is the core cyclic peptide or core antibiotic of laspartomycin, zaomycin, crystallomycin, aspartocin, amphomycin, glumamycin, brevistin, cerexin A, cerexin B, Antibiotic A-30912, Antibiotic A-1437, Antibiotic A-54145, Antibiotic A-21978C or tsushimycin. More preferably, R is the core antibiotic or core cyclic peptide of laspartomycin, aspartocin, Antibiotic A-30912, Antibiotic A-1437, Antibiotic A-54145 or Antibiotic A-21978C. Most preferably, R is the core antibiotic or core cyclic peptide of laspartomycin or aspartocin.

In another preferred embodiment, m is 0. In this embodiment, the antimicrobial sulfonamide derivative of the invention is represented by structural formula (III):

$$Y-SO_2N(R^4)-R \quad (III)$$

Here, the nitrogen atom covalently bonded to $R^4$ is directly attached to the core cyclic peptide or core antibiotic of a lipopeptide antibiotic (see section 4.1). Preferred embodiments of R and $R^4$ include those defined above. Particularly preferred embodiments include those where $R^4$ is hydrogen and/or R is the core antibiotic or core cyclic peptide of laspartomycin or aspartocin. In one preferred embodiment of compounds of Formula (III), Y is hexadec-yl, $R^4$ is H and R is the core antibiotic of laspartomycin or the t-butyl ester of the core antibiotic of laspartomycin.

Generally, the lipophilic group Y will be hydrophobic and when substituted will be substituted with hydrophobic substituents. Those of skill in the art will appreciate that the size and/or length of the lipophilic group will depend, in part, on the nature of fragments such as L, X, $R^1$, $R^4$ and R that comprise the antimicrobial sulfonamide derivative.

Preferably, the lipophilic group Y is selected from the group consisting of ($C_2$–$C_{30}$) alkyl optionally substituted with one or more of the same or different $R^7$ groups, ($C_2$–$C_{30}$) heteroalkyl optionally substituted with one or more of the same or different $R^7$ groups, ($C_5$–$C_{30}$) aryl optionally substituted with one or more of the same or different $R^7$ groups, ($C_5$–$C_{30}$) arylaryl optionally substituted with one or more of the same or different $R^7$ groups, ($C_5$–$C_{30}$) biaryl optionally substituted with one or more of the same or different $R^7$ groups, five to thirty membered heteroaryl optionally substituted with one or more of the same or different $R^7$ groups, ($C_6$–$C_{30}$) arylalkyl optionally substituted with one or more of the same or different $R^7$ groups and six to thirty membered heteroarylalkyl optionally substituted with one or more of the same or different $R^7$ groups;

each $R^7$ is independently selected from the group consisting of —$OR^8$, —$SR^8$, —$NR^8R^8$, —CN, —$NO_2$, —$N_3$, —C(O)$OR^3$, —C(O)$NR^8R^8$, C(S)$NR^8R^8$, —C($NR^8$)$NR^8R^8$, —CHO, —$R^8$CO, —$SO_2R^8$, —$SOR^8$, —PO($OR^8$)$_2$, —PO($OR^8$), —$CO_2H$, —$SO_3H$, —$PO_3H$, halogen and trihalomethyl;

each $R^8$ is independently selected from the group consisting of hydrogen, ($C_1$–$C_6$) alkyl, ($C_5$–$C_{10}$) aryl, five to fifteen membered heteroaryl, ($C_6$–$C_{16}$) arylalkyl and six to sixteen membered heteroarylalkyl.

The nature of the fragments such as L, X, $R^1$, $R^4$ and R that comprise the antimicrobial sulfonamide derivative are particularly important in defining preferred embodiments of the lipophilic fragment Y. Those of skill in the art will realize that preferred embodiments of Y will particularly depend on the core cyclic peptide or core antibiotic and/or the linker L. Accordingly, antimicrobial sulfonamide derivatives with different core cyclic peptides or core antibiotics and/or linkers L will have different preferred embodiments of the lipophilic fragment Y.

For example, when m is 0, X is —$SO_2$, $R^4$ is previously defined, and R is the core antibiotic of anhydro-Antibiotic-21987C or isomer-Antibiotic-21987 (or amino protected versions, thereof) preferred embodiments of Y include those described in Baker et al., U.S. Pat. No. 5,912,226. Preferred embodiments of Y described in Baker et al., U.S. Pat. No. 5,912,226 are preferred embodiments in the current invention, when the lipophilic group Y is connected by a sulfonamide linkage to the core antibiotic of anhydro-Antibiotic-21987C or isomer-Antibiotic-21987.

Alternatively, when m is 0, X is —$SO_2$—, $R^4$ is as previously defined and R is the core antibiotic of Antibiotic-21987C (or an amino protected version thereof) preferred embodiments of the lipophilic fragment Y include those described by the Lilly group (Debono, U.S. Pat. No. RE32, 333; Debono, U.S. Pat. No. RE32,311; Abbott et al., U.S. Pat. No. 4,537,717; Abbott et al., U.S. Pat. No. 4,524,135; Abbott et al., U.S. Pat. No. 4,482,487; Debono U.S. Pat. No. 4,399,067; Debono U.S. Pat. No. 4,396,543).

When m is 0, X is —$SO_2$—, $R^4$ is as previously defined and R is the core antibiotic of laspartomycin, preferred embodiments of Y include those described in Borders et al., U.S. patent application Ser. No. 09/760,328.

When m is 0, X is —$SO_2$—, $R^4$ is as previously defined and R is the core antibiotic of Antibiotic A-1437 preferred embodiments of Y include those described in Lattrell et al., U.S. Pat. No. 5,629,288. Similarly, when m is 1, X is —$SO_2$— and —CO—, $R^1$ and $R^4$ is as previously defined, L is the des-amino derivative of asparagine and R is the core antibiotic of Antibiotic A-1437, preferred embodiments of Y may be found in Lattrell et al., U.S. Pat. No. 5,629,288.

When m is 0, X is —$SO_2$—, $R^4$ is as previously defined and R is the core antibiotic of Antibiotic A54145, preferred embodiments of Y include those described in Fukada et al., U.S. Pat. No. 5,028,590 and Fukada et al., U.S. Pat. No. 5,039,789.

It will be understood that the selection of Y is intimately related to the structure of the core antibiotic or core cyclic peptide and linker. Given the structure of the core antibiotic or core cyclic peptide and linker, selection of preferred embodiments of Y is well within the purview of those of ordinary skill in the art given the examples provided above.

Particularly preferred antimicrobial sulfonamides include the following compounds.

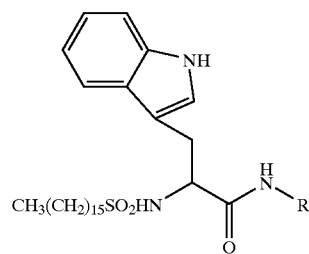

52

R is the core antibiotic of laspartomycin

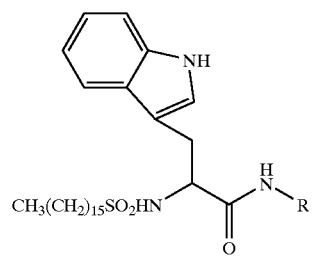

54

R is the core cyclic peptide of laspartomycin

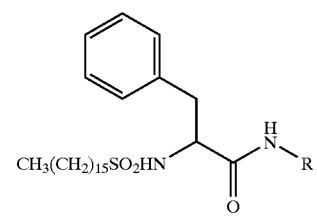

56

R is the core antibiotic of laspartomycin

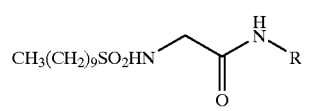

58

R is the core antibiotic of aspartocin

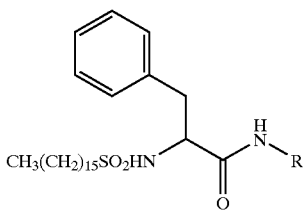

R is the FMOC derivative of the core antibiotic of aspartocin

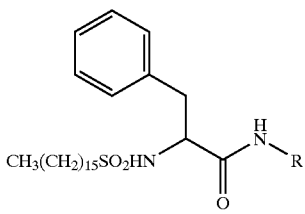

R is the core antibiotic of aspartocin 4.2.2 Methods of Making Antimicrobial Sulfonamide Derivatives Antimicrobial sulfonamide derivatives are preferably synthesized from amino antibiotics or core cyclic peptides, which may be made by the approaches described in Section 4.5 of this Application. Those of skill in the art will appreciate antimicrobial sulfonamide derivatives may be synthesized from a vast number of other different starting materials.

Starting materials useful for preparing antimicrobial sulfonamide derivatives from core antibiotics or core cyclic peptides are either commercially available or may be prepared by conventional synthetic methods. A number of general synthetic approaches may be envisioned for converting core antibiotics or core cyclic peptides to antimicrobial sulfonamide derivatives. These include, but are not limited to, the approaches outlined in Schemes I–IV.

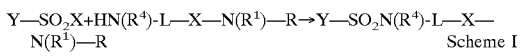
Scheme I

In Scheme I, an activated lipophilic sulfonyl derivative $(Y—SO_2X)$ is reacted with a free amino group $(HN(R^4))$ attached to a linker (L) to form the sulfonamide linkage.

In Scheme II, an activated lipophilic sulfonyl derivative $(Y—SO_2X)$ is reacted with a free amino group $(HN(R^1))$ attached to a core cyclic peptide or to a core antibiotic to form the sulfonamide linkage.

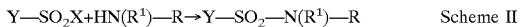
Scheme II

In both Scheme I and Scheme II, activated lipophilic sulfonyl derivative Y—SO₂X takes the same form. Here, X may be an activated derivative, such as, for example, halogen (e.g., fluoride, bromide, chloride or iodide) or active ester (e.g., pentaflourophenyl ester, N-hydroxy succinimide ester, p-nitrophenylester, etc.). Preferably, X is a hydroxybenzotriazole ester or a sulfonyl chloride. Alternatively, X may be OH, which is activated in situ by well known methods (aminium salts, uronium salts, carbodiimides, etc.) Methods for constructing the sulfonamide linkage are well-known to the skilled artisan and may be found in compendiums of synthetic methods (*Beilstein Handbook of Organic Chemistry*, Beilstein Institute of Organic Chemistry, Frankfurt, Germany; Feiser, L.; Feiser, M., *Reagents for Organic Synthesis*, Volumes 1–17, Wiley Interscience; Trost, B.; Fleming, I, *Comprehensive Organic Synthesis*, Pergamon Press, 1991; *Theilheimer's Synthetic Methods of Organic Chemistry*, Volumes 1–45, Karger, 1991; *Compendium of Organic Synthetic Methods*, Wiley Interscience, Volumes 1–7; March, J., *Advanced Organic Chemistry*, Wiley Interscience, 1991; Larock, R.; *Comprehensive Organic Transformations*, VCH Publishers, 1989; Paquette, L. (ed.), *Encyclopedia of Reagents for Organic Synthesis*, John Wiley & Sons, 1995).

Those of skill in the art will appreciate that protection of reactive functionalities in Y, $R^1$, $R^4$, L and R may be necessary for formation of the sulfonamide linkage. In the event that protection of Y, $R^1$, $R^4$, L and R is necessary to form the sulfonamide bond, then deprotection of Y, $R^1$, $R^4$, L and R will be necessary to provide the desired antimicrobial sulfonamide derivative. Methods for protection and deprotection of organic groups are known to those of skill in the art and may be used as necessary in the synthesis of antimicrobial sulfonamide derivatives (see e.g., Greene, T. W.; Wuts, P., *Protective Groups in Organic Synthesis*, $3^{rd}$ edition, Wiley Interscience, 1999).

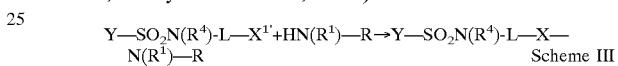
Scheme III

In Scheme III, lipophilic fragment Y and linker L, attached via a sulfonamide bond, are covalently linked to, for example, a sulfonic or carboxylic acid or an activated derivative thereof (i.e., $X^1$) such as an active ester or a halogen. Sulfonic acids and carboxylic acids may be activated in situ by methods known to the skilled artisan (e.g., uronium salts, phosphonium salts, carbodiimides, etc.). Methods for making activated derivatives of carboxylic acids and sulfonic acids and reacting these derivatives with amines to form amides or sulfonamides are known to those of skill in the art. Preferably, $X^{1'}$ is a hydroxybenzotriazole ester or a chloro derivative of a sulfonic or carboxylic acid. Linkages other than sulfonamides or carboxamides may be formed by methods known to those of skill in the art.

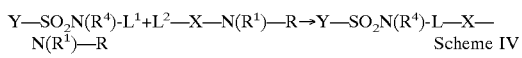
Scheme IV

Scheme IV describes a convergent approach where $Y—SO_2N(R^4$-L—X—N(R^1)$—R is synthesized by combining two fragments $(Y—SO_2N(R^4)$-$L^1$ and $L^2$—X—N(R^1)$—R) to form the antimicrobial sulfonamide derivative. Here $L^1$ and $L^2$ combine to form the linker L upon covalent bond formation. Such an approach may be particularly useful when L is an oligomer such as a polyamide or polyethers. Methods for combining oligomeric subunits such as ether or amide monomers, dimers, etc. are known to those of skill in the art (Bodanzsky, M., *Principles of Peptide Synthesis*; Springer Verlag, 1984; Bodanzsky, M., *Practice of Peptide Synthesis*; Springer Verlag, 1984). Fragment $Y—SO_2N(R^4)$-$L^1$ may be made by forming a sulfonamide bond between $Y—SO_2X$ and $HN(R^4)$-$L^1$ using methods described above. Fragment $L^2$—X—N(R^1)$—R may be made, as described above, by forming either a sulfonamide bond or an amide between $L^2$—$X^{1'}$ and $HN(R^1)$—R, where $X^{1'}$ is either a carboxylic acid or a sulfonic acid or activated derivatives thereof.

4.2.3 Methods of Obtaining Amino Core Cyclic Peptides and Amino Core Antibiotics Culturing microorganisms that yield acidic lipopeptide antibiotics may be used to provide amino core antibiotics or amino core cyclic peptides that can be converted to antimicrobial sulfonamide derivatives. Microorganisms that synthesize acidic lipopeptide antibiotics are well known in the art (see e.g., Umezawa et al., U.S. Pat. No. 3,639,582; Debono et. al., 1988, *J. Antibiotics,* 41, 1093; Shay et al., 1960, *Antibiotics Annual,* 194; Hamill et al., U.S. Pat. No. 4,331,594; Hamill et al., U.S. Pat. No. 4,208,403; Hoehn et al., U.S. Pat. No. 4,024,245; Higgins et al., U.S. Pat. No. 4,024,246; Boeck et al., U.S. Pat. No. 4,288,549; Boeck et al., U.S. Pat. No. 4,994,270; Boeck, U.S. Pat. No. 4,977,083). Methods of growing inocula and inoculating culturing medium are known to the skilled artisan and exemplary methods have been described in the art. Id. Preferred media, times, temperatures and pH for culturing microorganisms that yield acceptable amounts of acidic lipopeptide antibiotics are also known in the art. Id.

Preferably, acidic lipopeptide antibiotics produced by culturing microorganisms are purified from fermentation broth or culture medium using extractive methods. The acidic lipopeptide antibiotic may be isolated as either the free acid or the salt.

Alternatively, lipopeptide antibiotics may be purified and isolated from fermentation broth or culture medium by any art-known technique such as high performance liquid chromatography, counter current extraction, centrifugation, filtration, precipitation, ion exchange chromatography, gel electrophoresis, affinity chromatography and the like, either before or after extractive purification using the methods of the current invention. The actual conditions used to purify a lipopeptide antibiotics will depend, in part, on factors such as net charge, hydrophobicity, hydrophilicity, etc., and will be apparent to those having skill in the Generally, the lipophilic fragment of the acidic lipopeptide antibiotic is enzymatically cleaved to provide the core antibiotic or core cyclic peptide. Addition of an appropriate enzyme to the culture medium may provide the core antibiotic or core cyclic peptide directly, thus obviating the need to isolate the lipopeptide antibiotic (Kreuzman et al., U.S. Pat. No. 5,573,936). Alternatively, the lipopeptide antibiotic may be chemically deacylated to provide the core antibiotic or core cyclic peptide, although this method frequently leads to complex mixtures (see e.g., Shoji et al., *J. Antibiotics* 28, 764, 1975; Shoji et al., *J. Antibiotics* 29, 380, 1976; Shoji et al., *J. Antibiotics* 29, 1268, 1976; Shoji et al., *J. Antibiotics* 29, 1275, 1976).

Preferably, isolated lipopeptide antibiotics are treated with an enzyme that removes at least the lipophilic fragment of the lipopeptide antibiotic. The enzyme may be, for example, a degradative enzyme such as a peptidase, esterase or thiolase, of which numerous examples exist in the art (Chihahra et al., *Agr. Biol. Chem.* 38, 1767, 1974; Suzuki et al., *J. Biochem.,* 56, 335, 1964; Konishi et al., U.S. Pat. No. 5,079,148). Preferably, the enzyme is a deacylase (Abbot et al., U.S. Pat. No. 4,299,763; Abbot et al., U.S. Pat. No. 4,299,762; Abbot et al., U.S. Pat. No. 4,293,490; Kleinschmidt et al., U.S. Pat. No. 3,150,059; Abbott et al., U.S. Pat. No. 4,293,482; Kimura et al., Japanese Patent No. 4058/67; Kuwana et al., U.S. Pat. No. 4,050,989; Shoji et al., *J. Antibiotics* 28, 764, 1975; Shoji et al., *J. Antibiotics* 29, 380, 1976; Shoji et al., *J. Antibiotics* 29, 1268, 1976; Shoji et al., *J. Antibiotics* 29, 1275, 1976).

Preferably, the cleavage of lipopeptide antibiotics to core antibiotics or core cyclic peptides commences by culturing microorganisms that produces a deacylase. The lipopeptide antibiotic is then contacted with the culture medium containing the deacylase. Microorganisms such as those of the Actinoplanacae that produce deacylases are well known to those of skill in the art. In a preferred embodiment, the microorganism *Actinoplanes utahensis* (NRRL 12052) provides a deacylase that deacylates many lipopeptide antibiotics to yield core antibiotics or core cyclic peptides (see e.g., Lattrell et al., U.S. Pat. No. 5,039,789; Fukuda et al., U.S. Pat. No. 5,039,789; Abbott et al., U.S. Pat. No. 4,320,054; Abbott et al., U.S. Pat. No. 4,537,717; Debono et al., U.S. Pat. No. 4,293,483; Borders et al., U.S. Pat. No. 6,511,962).

Parent cultures of *Actinoplanes utahensis* (NRRL 12052) especially suitable for cleaving the lipophilic fragment of lipopeptide antibiotics may be selected by methods known to those of skill in the art. A preferred method for selecting a parent culture which provides improved yields of core antibiotics or core cyclic peptides is described in Section 5.1

Growing inocula and inoculating culturing medium are also well known to those of skill in the art and exemplary methods for *Actinoplanes utahensis* (NRRL 12052) are described in the art (see e.g., Boeck et al., 1988, *J. Antibiot.,* 41, 1085; Debono et. al., 1988, *J. Antibiotics,* 41, 1093; Lattrell et al., U.S. Pat. No. 5,039,789; Fukada et al., U.S. Pat. No. 5,039,789; Abbott et al., U.S. Pat. No. 4,320,054; Abbott et al., U.S. Patent No. 4,537,717; Debono, U.S. Pat. No. 4,293,483) and Section 5.1.

Any culturing medium which supports *Actinoplanes utahensis* (NRRL 12052) growth may be used and selection of such medium is within the capability of those of skill in the art. Representative examples of culturing medium which supports *Actinoplanes utahensis* (NRRL 12052) growth may be found in the art (see e.g., Boeck et al., 1988, *J. Antibiot.,* 41, 1085; Debono et. al., 1988, *J. Antibiotics,* 41, 1093; Lattrell et al., U.S. Pat. No. 5,039,789; Fukada et al., U.S. Pat. No. 5,039,789; Abbott et al., U.S. Pat. No. 4,320,054; Abbott et al., U.S. Pat. No. 4,537,717; Debono, U.S. Pat. No. 4,293,483) and Section 5.1.

Preferred media, times, temperatures and pH for culturing *Actinoplanes utahensis* (NRRL 12052) that provide good yields of the deacylase are described in the art (see e.g., Boeck et al., 1988, *J. Antibiot.,* 41, 1085; Debono et. al., 1988, *J. Antibiotics,* 41, 1093; Lattrell et al., U.S. Pat. No. 5,039,789; Fukada et al., U.S. Pat. No. 5,039,789; Abbott et al., U.S. Pat. No. 4,320,054; Abbott et al, U.S. Pat. No. 4,537,717; Debono, U.S. Pat. No. 4,293,483) and Section 5.2.3.

Representative procedures for deacylating lipopeptide antibiotics with *Actinoplanes utahensis* (NRRL 12052) to provide core antibiotics or core cyclic peptides may be found in the art (see e.g., Boeck et al., 1988, *J. Antibiot.,* 41, 1085; Debono et. al., 1988, *J. Antibiotics,* 41, 1093; Lattrell et al., U.S. Pat. No. 5,039,789; Fukada et al., U.S. Pat. No. 5,039,789; Abbott et al., U.S. Pat. No. 4,320,054; Abbott et al., U.S. Pat. No. 4,537,717; Debono, U.S. Pat. No. 4,293,483) and Example 4.

Although, deacylation of lipopeptide antibiotics such as aspartocin, A-30912, A-21978C and laspartomycin with *Actinoplanes utahensis* (NRRL 12052) has been successful it should be pointed out that other procedures may be necessary for other lipopeptide antibiotics. Enzymes possess a high degree of specificity and slight differences in the peptide moiety or the lipophilic fragment may have a profound effect on the rate of deacylation. Further, in some situations (i.e., Antibiotic A-30912 and Antibiotic A-21978C) the lipophilic fragment may be selectively removed to provide the core antibiotic. In other situations (i.e., laspartomycin) cleavage of the lipophilic fragment is accompanied by hydrolysis of exocyclic peptide bonds to provide the core cyclic peptide. Thus, deacylation of lipopeptide antibiotics with a deacylase may provide a number of different peptide products.

Alternatively, core antibiotics or core cyclic peptides may be produced by methods known in the art for synthesizing peptides. For example, linear peptides may be prepared using conventional solution phase or solid phase peptide synthesis and then cyclized.

Core antibiotics or core cyclic peptides may be purified and isolated from either fermentation broth or synthetic reaction mixtures by any art-known technique such as high performance liquid chromatography, counter current extraction, centrifugation, filtration, precipitation, ion exchange chromatography, gel electrophoresis, affinity chromatography and the like. The actual conditions used to purify a particular core antibiotic or core cyclic peptide will depend, in part, on factors such as net charge, hydrophobicity, hydrophilicity, etc. and will be apparent to those having skill in the art. 4.2.4 Activity Generally, active antimicrobial sulfonamide derivatives of the invention are identified using in vitro screening assay. Indeed, in many instances the antimicrobial sulfonamide derivatives of the invention will be used in vitro as preservatives, topical antimicrobial treatments, etc. Additionally, despite certain apparent limitations of in vitro susceptibility tests, clinical data indicate that a good correlation exists between minimal inhibitory concentration (MIC) test results and in vivo efficacy of antibiotic compounds (Murray, 1994, *Antimicrobial Susceptibility Testing*, Poupard et al., eds., Plenum Press, NY; Knudsen et al., 1995, *Antimicrob. Agents Chemother.* 39(6):1253–1258). Thus, isolated antimicrobial sulfonamide derivatives useful for treating infections and diseases related thereto are also conveniently identified by demonstrated in vitro antimicrobial activity against specified microbial targets.

Generally, the in vitro antimicrobial activity of antimicrobial agents is tested using standard NCCLS bacterial inhibition assays, or MIC tests (see, National Committee on Clinical Laboratory Standards "Performance Standards for Antimicrobial Susceptibility Testing," NCCLS Document M100-S5 Vol. 14, No. 16, December 1994; "Methods for dilution antimicrobial susceptibility test for bacteria that grow aerobically—Third Edition," Approved Standard M7-A3, National Committee for Clinical Standards, Villanova, Pa.).

Alternatively, the antimicrobial sulfonamide derivatives of the invention may be assessed for antimicrobial activity using in vivo models. Again, such models are well-known in the art.

It will be appreciated that other assays, as are well known in the art or that will become apparent to those having skill in the art upon review of this disclosure, may also be used to identify active antimicrobial sulfonamide derivatives of the invention. Such assays include, for example, the assay described in Lehrer et al., 1988, *J. Immunol. Methods* 108:153 and Steinberg et al., "Designer Assays for Antimicrobial Peptides: Disputing the 'One Size Fits All' Theory," *In: Antibacterial Peptide Protocols*, Shafer, Ed., Humana Press, NJ.

Generally, antimicrobial sulfonamide derivatives of the invention will exhibit MICs of less than about 64 µg/mL, usually less than about 32 µg/mL, preferably less than about 16 µg/mL and most preferably less than about 4 µg/mL. The antimicrobial sulfonamide derivatives of the invention may also exhibit antifungal activity, having MICs of about 50 µg/mL or less against a variety of fungi in standard in vitro assays.

Of course, compounds having MICs on the low end of these ranges, or even lower, are preferred. Most preferred for use in treating or preventing systemic infections are antimicrobial sulfonamide derivatives that exhibit significant antimicrobial activity (i.e., less than 4 µg/mL), good water-solubility (at approx. neutral pH) and low toxicity. Toxicity is less of a concern for topical administration, as is water solubility.

4.2.5 Compositions and Uses

The antimicrobial sulfonamide derivatives of the invention can be used in a wide variety of applications to inhibit the growth or kill microorganisms. For example, the antimicrobial sulfonamide derivatives may be used as disinfectants or as preservatives for materials such as foodstuffs, cosmetics, medicaments and other nutrient containing materials. The antimicrobial sulfonamide derivatives can also be used to treat or prevent diseases related to microbial infection in subjects such as plants and animals.

For use as a disinfectant or preservative, the antimicrobial sulfonamide derivatives can be added to the desired material singly, as mixtures of antimicrobial sulfonamide derivatives or in combination with other antifungal and/or antimicrobial agents. The antimicrobial sulfonamide derivatives may be supplied as the compound per se or may be in admixture with a variety of adjuvants, carriers, diluents or excipients, which are well known in the art.

When used to treat or prevent microbial infections or diseases related thereto, the antimicrobial sulfonamide derivatives of the invention can be administered or applied singly, as mixtures of two or more antimicrobial sulfonamide derivatives, in combination with other antifungal, antibiotic or antimicrobial agents or in combination with other pharmaceutically active agents. The antimicrobial sulfonamide derivatives can be administered or applied per se or as pharmaceutical compositions. The specific pharmaceutical formulation will depend upon the desired mode of administration, and will be apparent to those having skill in the art. Numerous compositions for the topical or systemic administration of antibiotics are described in the literature. Any of these compositions may be formulated with the antimicrobial sulfonamide derivatives of the invention.

Pharmaceutical compositions comprising the antimicrobial sulfonamide derivatives of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable adjuvants, carriers, diluents, excipients or auxiliaries which facilitate processing of the active antimicrobial sulfonamide derivatives into preparations which can be used pharmaceutically. Proper formulation is dependent upon the route of administration chosen.

For topical administration the antimicrobial sulfonamide derivatives of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the antimicrobial sulfonamide derivatives of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the antimicrobial sulfonamide derivatives may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the antimicrobial sulfonamide derivatives can be readily formulated by combining them with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compositions may take the form of tablets, lozenges, etc. formulated in conventional manner.

For administration by inhalation, the compounds of the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The antimicrobial sulfonamide derivatives may also be formulated in rectal or vaginal compositions such as suppositories or retention enemas, e.g., containing conventional suppository bases such as cocoa butter or other glycerides.

In addition to the formulations described previously, the antimicrobial sulfonamide derivatives may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver the antimicrobial sulfonamide derivatives of the invention. Certain organic solvents such as dimethylsulfoxide also may be employed, although usually at the cost of greater toxicity. Additionally, the antimicrobial sulfonamide derivatives may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days.

As certain of the carboxylic acids of the antimicrobial sulfonamide derivatives of the invention are acidic, or the lipophilic group or linker may include acidic or basic substituents, the antimicrobial sulfonamide derivatives may be included in any of the above-described formulations as the free acids, the free bases or as pharmaceutically acceptable salts.

The antimicrobial sulfonamide derivatives of the invention, or compositions thereof, will generally be used in an amount effective to achieve the intended purpose. Of course, it is to be understood that the amount used will depend on the particular application.

For example, for use as a disinfectant or preservative, an antimicrobially effective amount of a antimicrobial sulfonamide derivative, or composition thereof, is applied or added to the material to be disinfected or preserved. By antimicrobially effective amount is meant an amount of antimicrobial sulfonamide derivative or composition that inhibits the growth of, or is lethal to, a target microbe. While the actual amount will depend on a particular target microbe and application, for use as a disinfectant or preservative the antimicrobial sulfonamide derivatives, or compositions thereof, are usually added or applied to the material to be disinfected or preserved in relatively low amounts. Typically, the antimicrobial sulfonamide derivatives comprises less than about 5% by weight of the disinfectant solution or material to be preserved, preferably less than about 1% by weight and more preferably less than about 0.1% by weight. An ordinarily skilled artisan will be able to determine antimicrobially effective amounts of particular antimicrobial sulfonamide derivatives for particular applications without undue experimentation using, for example, the in vitro assays provided in the examples.

For use to treat or prevent microbial infections, the antimicrobial sulfonamide derivatives of the invention, or compositions thereof, are administered or applied in a therapeutically effective amount. By therapeutically effective amount is meant an amount effective to ameliorate the symptoms of, or ameliorate, treat or prevent microbial infections. Determination of a therapeutically effective amount is well within the capabilities of those skilled in the art, especially in light of the detailed disclosure provided herein. Preferably, a therapeutically effective amount is between about 20 mg/kg and about 0.5 mg/kg, more preferably between about 10 mg/kg and about 1 mg/kg, most preferably between about 5 mg/kg and about 2 mg/kg.

As in the case of disinfectants and preservatives, a therapeutically effective dose, for topical administration to treat or prevent microbial, yeast, fungal or other infection, can be determined using conventional methods by the skilled artisan. The treatment may be applied while the infection is visible, or even when it is not visible. An ordinarily skilled artisan will be able to determine therapeutically effective amounts to treat topical infections without undue experimentation.

For systemic administration, a therapeutically effective dose can be estimated initially from in vitro assays. For example, a dose can be formulated in animal models to achieve a circulating antimicrobial sulfonamide derivative concentration range that includes the $IC_{50}$ as determined in cell culture (i.e., the concentration of test compound that is lethal to 50% of a cell culture), the MIC as determined in cell culture (i.e., the minimal inhibitory concentration for growth) or the $IC_{100}$ as determined in cell culture (i.e., the concentration of antimicrobial sulfonamide derivative that is lethal to 100% of a cell culture). Such information can be used to more accurately determine useful doses in humans.

Initial dosages can also be estimated from in vivo data (e.g., animal models) using techniques that are well known in the art. One of ordinary skill in the art can readily optimize administration to humans based on animal data.

Alternatively, initial dosages can be determined from the dosages administered of known antimicrobial agents (e.g., aspartocin, laspartomycin etc.) by comparing the $IC_{50}$, MIC and/or $I_{100}$ of the specific antimicrobial sulfonamide derivatives with that of a known antimicrobial agent, and adjusting the initial dosages accordingly. The optimal dosage may be obtained from these initial values by routine optimization.

Dosage amount and interval may be adjusted individually to provide plasma levels of the active antimicrobial sulfonamide derivatives which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering a single daily dose or multiple doses each day.

In cases of local administration or selective uptake, the effective local concentration of antimicrobial sulfonamide derivative may not be related to plasma concentration. One having skill in the art will be able to optimize therapeutically effective local dosages without undue experimentation.

The amount of antimicrobial sulfonamide derivative administered will, of course, be dependent on, among other factors, the subject being treated, the subject's weight, the severity of the affliction, the manner of administration and the judgment of the prescribing physician.

The antimicrobial therapy may be repeated intermittently while infections are detectable, or even when they are not detectable. The therapy may be provided alone or in combination with other drugs, such as for example other antibiotics or antimicrobials, or other antimicrobial sulfonamide derivatives of the invention.

Preferably, a therapeutically effective dose of the antimicrobial sulfonamide derivatives described herein will provide therapeutic benefit without causing substantial toxicity. Toxicity of the antimicrobial sulfonamide derivatives can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Antimicrobial sulfonamide derivatives which exhibit high therapeutic indices are preferred. The data obtained from these cell culture assays and animal studies can be used in formulating a dosage range that is not toxic for use in subjects. The dosage of the antimicrobial sulfonamide derivatives described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g., Fingl et al., 1975, In: The Pharmacological Basis of Therapeutics, Ch.1, p.1).

5. EXAMPLES

The invention having been described, the following examples are presented to illustrate, rather than limit, the scope of the invention. The examples illustrate various embodiments and features of the present invention.

5.1 Preparation of Deacylase Enzyme

The deacylase is produced by culturing *Actinoplanes utahensis* NRRL 12052 under submerged aerobic fermentation conditions. Because single-colony isolates from a lyophile of the culture were heterogeneous for both morphology and enzyme production capability, selections were made to recover a stable, high-producing variant. Initially, multiple fermentations were carried out using inocula prepared from strain 12052. Vegetative growth from the flask yielding high deacylating activity was plated on a differential agar (CM). Colonies were then selected for further evaluation. Generally, small colony types were better enzyme producers than large colony types. Isolate No. 18 was the best deacylase producer of all selected colonies and was routinely used for the production of the deacylase enzyme. CM agar contained corn steep liquor 0.5%, Bacto peptone 0.5%, soluble starch 1.0%. NaCl 0.05%, $CaCl_2.2H_2O$ 0.05% and Bacto agar 2.0%.

The high-producing, natural variant was used in the known fermentation protocol employed (Boeck et al., 1988. *J. Antibiot.*, 41, 1085). A stock culture of *Actinoplanes utahensis* NRRL 12052 variant, preserved in 20% glycerol at −70° C., was introduced into a 25×150 mm test tube containing 10 mL of a medium comprised of 2.0% sucrose, 2.0% pre-cooked oatmeal, 0.5% distiller's grain, 0.25% yeast, 0.1% $K_2HPO_4$, 0.05% KCl, 0.05% $MgSO_4$-$7H_2O$ and 0.0002% $FeSO_4$-$7H_2O$ in deionized water. After incubation at 30° C. for 72 hrs on a rotary shaker orbiting at 250 rpm the resulting mycelial suspension was transferred into 50 mL of PM3 medium in a 250 mL Erlenmeyer flask. The PM3 medium contained 2.0% sucrose, 1.0% peanut meal, 0.12% $K_2HPO_4$, 0.05% $KH_2PO_4$ and 0.025% $MgSO_4$-$7H_2O$, in tap water. The flask was incubated at a temperature of 30° C. for a period of between 60 to 90 hrs. The whole broth from this fermentation contained the deacylase enzyme.

5.2 Synthesis of Decanesulfonylglycyl Aspartocin

5.2.1 Extractive Purification of Aspartocin

Approximately 20 grams of a crude preparation of aspartocin (see e.g., Shay et al., 1960, *Antibiotics Annual*, 194) was mixed with about 125 mL of water and insoluble impurities were separated by centrifugation. About 300 mg of $CaCl_2$ was added to the brown colored liquid and the resulting solution was adjusted to a pH of between about 8.6 to about pH 9.0. Aspartocin was then extracted into about 100 mL of 1-butanol. The aqueous phase was again mixed with about 600 mg of $CaCl_2$ and then extracted with 1-butanol. The combined butanol extracts were mixed with an equal amount of water, the mixture adjusted to about pH 2.0 and the butanol phase washed with about 160 mL of water adjusted to approximately pH 2.0. Aspartocin, was then extracted into water at about pH 7.0 and then back into butanol at a pH of between about pH 2.0 to about pH 3.0. The butanol phase was washed with about 100 mL of water at approximately pH. 2.0, then combined with an equal volume of water and adjusted to about pH 7.0. The pH adjustments were made with 1 N HCl and 1 N NaOH. The aqueous phase is evaporated under vacuum to remove residual butanol. The very slightly colored clear liquid was freeze-dried to obtain 803 mg of the sodium salt of aspartocin as tan-white powder. FAB-MS m/z:1340 $(M+Na)^+$, 1362 $(M+2Na-H)^+$, 1384 $(M+3Na-2H)^+$, 1406 $(M+4Na-3H)^+$.

5.2.2 Preparation of FMOC-Aspartocin

Aspartocin (0.54 g, 0.41 mmol) preferably purified as described in Section 5.2.1, and 0.30 mL (1.73 mmol) of diisopropylethylamine were dissolved in 5 mL of $H_2O$, cooled in an ice bath. 9-fluorenylmethyloxycarbonyl ("FMOC") chloride, 0.26 g (1.0 mmol) was dissolved in 2.0 mL of dioxane and 1.0 mL of this solution added to the cooled aspartocin solution. High Pressure Liquid Chromatography ("HPLC") analysis indicated that the reaction was almost complete after 0.5 hour, at which time the remaining 1.0 mL of FMOC chloride solution was added to the reaction mixture. After 15 minutes 6 mL of $H_2O$ was added and the reaction mixture was extracted twice with ethyl acetate ("EtOAc").

The aqueous phase was filtered through Celite, evaporated to remove residual EtOAc, and freeze-dried to obtain 0.56 g of product. The salt was then dissolved in 15 mL of $H_2O$, centrifuged to remove a small amount of insoluble material, acidified to pH 1.88 with 1 N HCl, separated from the acidified solution by centrifugation, washed with $H_2O$, and dried in vacuo over $P_2O_5$ to yield 0.31 g of the free acid. FAB-MS of the major component had m/z 1542 $(M+H)^+$.

5.2.3 Deacylation of FMOC-Aspartocin

FMOC-aspartocin (476 mg of about 65% purity) prepared as described in Section 5.2.2 was dissolved in 30 mL of 0.5 M potassium phosphate buffer, pH 7.1, to which 300 mL of deacylase fermentation broth was added. The reaction mixture was incubated for about 18 hours at about 29° C. Conversion of FMOC-Aspartocin to the deacylated product was estimated to be about 72% complete by HPLC analysis. Acetonitrile (150 mL) was added to the fermentation broth, the mixture sonicated for about 1 minute, centrifuged at 3000 rpm for 5 minutes and decanted. The decanted supernatant was diluted with an equal volume of distilled water (total volume about 900 mL), split into three equal portions, and applied to three styrene-divinylbenzene resin cartridges (ENVI-Chrom P resin, 3.1 g per cartridge, 25×30 mm). The cartridges were eluted by gravity flow using a stepwise gradient in acetonitrile buffered with 0.025 M potassium phosphate at pH 7.1. The deacylated product was eluted with a 23–27% acetonitrile gradient. Appropriate fractions were pooled and acetonitrile removed under vacuum at room temperature. The three resin cartridges were regenerated by elution with acetonitrile, followed by equilibration with 5% acetonitrile in unbuffered water and the pooled fractions were then applied to the cartridges. Excess salt was removed by washing with 5% acetonitrile, while the product was eluted with 50% acetonitrile. Acetonitrile was removed from the combined desalted product fractions under vacuum at room temperature and the fractions were freeze dried to yield 184 mg of an orange-tan solid, $C_{60}H_{79}N_{13}O_{21}$ of deacylated FMOC-aspartocin (i.e., the FMOC derivative of the amino core antibiotic of aspartocin). FAB-MS: m/z 1356$(M+K)^+$, 1394$(M-H+2K)^+$. Calculated for $C_{60}H_{79}N_{13}O_{21}$+K, 1356).

5.2.4 Sulfonation of Deacylated FMOC-Aspartocin

About 13.5 mg of deacylated FMOC-aspartocin (prepared as described in Section 5.2.3; approximately 65% pure as the major component) was dissolved in about 1.0 mL of dimethylformamide containing 0.01 mL of diisopropylethylamine. The hydroxybenzotriazole activated ester of decanesulfonylglycine was added incrementally to the above solution at room temperature and the reaction monitored by HPLC. After about 2.5 hours the conversion to product was estimated to be about 71% with the total amount of presumed product about 6 mg. The reaction mixture was poured over 4.0 g ice and the pH adjusted to about 6.7 by addition of 2 drops of $H_3PO_4$, 2 mL of 0.5M ammonium phosphate buffer pH 7.2 and 2 mL of acetonitrile. After storage in the freezer for about 3 days the thawed reaction mixture was diluted with 2 mL of 0.5 M acetate buffer (pH 4.6) and 4 mL of distilled water; the pH was adjusted to about pH 4.9 by addition of acetic acid to provide a slightly turbid solution. The solution was applied to a divinylbenzene-styrene resin cartridge (Supelco ENVI-Chrom P, 5.0 g, 25×40 mm) with gravity flow. The cartridge was eluted with a stepwise gradient of pH 4.6 acetate-buffered aqueous acetonitrile with the product being eluted with 45% acetonitrile. Fractions were pooled, acetonitrile removed under vacuum at room temperature and the resulting aqueous solution freeze dried to yield 5.5 mg of white solid. FAB-MS: m/z 1617$(M+K)^+$. Calculated for $C_{72}H_{102}N_{14}O_{24}S$+K, 1617.

5.2.5 Deprotection of Decanesulfonylglycyl-FMOC-Aspartocin

One drop of piperdine was added to about 5.5 mg of the product from Section 5.2.4 dissolved in 2.0 mL of 2:1 mixture of dimethylsulfoxide:methanol. Monitoring by HPLC indicated the reaction was complete after 60 minutes at room temperature. The reaction was quenched by addition of 6.0 mL cooled 0.2 M ammonium phosphate at pH 7.2. The quenched reaction mixture was applied to a 0.5 g resin cartridge (ENVI-Chrom P) and eluted with a stepwise gradient of pH 7.2 phosphate-buffered aqueous acetonitrile. The product was eluted with 25% acetonitrile. Appropriate fractions were pooled and acetonitrile was removed under vacuum at room temperature. The product was desalted by adsorption onto a 0.5 g resin cartridge which was then rinsed with 10% acetonitrile, followed by 50% acetonitrile. The 50% acetonitrile eluate was evaporated to remove acetonitrile and the resulting aqueous solution freeze dried to provide about 1.5 mg of white solid. FAB-MS: m/z 1379 $(M+Na)^+$ was consistent with the expected structure. The MIC values for the decanesulfonylglycyl derivative against *Staphylococcus aureus* were essentially the same as those for aspartocin.

5.2.6 Scale-Up of Sulfonation of Deacylated FMOC-Aspartocin

About 68 mg of deacylated FMOC-aspartocin (prepared as described in Section 5.2.3; approximately 65% pure as the major component) was dissolved in about 1.0 mL dimethylformamide. The HOBT activated ester of decanesulfonylglycine was added incrementally to the peptide solution and the reaction was monitored by HPLC until the conversion to product was about 95%. The total amount of presumed product was estimated to be about 32.0 mg. The reaction mixture was diluted with about 5 mL of methanol, the apparent pH adjusted to between about 6–7 using 1.5M $NH_4OH$ and then filtered through a 0.45 μm membrane. The filtrate was chromatographed on a Sephadex LH-20 size exclusion column, which was eluted with methanol. Fractions containing product were pooled and methanol was evaporated under vacuum to provide about 64 mg of solid residue, which contained about 29 mg of product. The partially purified product was deblocked by dissolving in about 2 mL of dimethylsulfoxide/methanol (2/1), adding 2 drops of piperidine and stirring at about 25° C. for 75 minutes. The reaction mixture was then diluted with about 20 mL of 10% acetonitrile buffered ammonium phosphate (apparent pH of about 7.8), and then filtered through a 0.45 μm membrane. The filtrate was applied to a 2.5×8.5 cm styrene-divinylbenzene resin column (Supelco ENVI-Chrom P, 9.3 g) and eluted with increasing concentrations of acetonitrile in aqueous ammonium phosphate at pH7.2. The presumed product was eluted in 30% acetonitrile. Appropriate fractions were pooled, the acetonitrile was evaporated under vacuum, and the solution was desalted and freeze dried in similar fashion as described in Section 5.2.4. Yield:

2 mg product of ca. 80% purity. Additional product was recovered by pooling side fractions from the resin column isolation and rechromatographing on a 5.0 g resin column; product was eluted with ca. 28% acetonitrile. Appropriate fractions were pooled and the desalted product was recovered in similar fashion as described above. The first 21 mg of product was added to the desalted rechromatographed side fractions pool and freeze dried. Overall yield: 29 mg of white solid of 80% purity based on HPLC, $C_{57}H_{92}N_{14}O_{22}S$, FABMS: m/z 1357, $(M+H)^+$, 1379$(M+Na)^+$, 1395$(M+K)^+$.

5.3 Synthesis of the Amino Core Antibiotic and Amino Core Cyclic Peptide of Laspartomycin

5.3.1 Biochemical Synthesis of the Amino Core Cyclic Peptide of Laspartomycin Laspartomycin (257 mg) in about 12 mL of 0.5M phosphate buffer of about pH 7.2 was added to about 120 mL of deacylase fermentation broth prepared as in Section 5.1 and incubated for about 16 hours at about 29° C. at about 180 rpm. The broth was centrifuged, the centrifugate decanted and solids were extracted with about 40 mL of distilled water. The pooled centrifugates were then applied to a 2.5×5.0 cm styrene-divinylbenzene resin column (ENVI™-Chrom P) and the product was eluted with a 10% and 11% acetonitrile-pH 7.2 phosphate mixture. Pooled fractions were concentrated and the pH was adjusted to about 4.65 by addition of ammonium acetate-acetic acid buffer. The fractions were then applied to a 2.5×5.0 cm resin column (ENVI™-Chrom P). The desired material was eluted with a 12.5% acetonitrile-ph 4.65 acetate mixture. The pH of the pooled fractions was adjusted to about 7.8, followed by concentration and freeze-dried to provide about 74 mg of the amino core cyclic peptide of laspartomycin as an off-white solid which was about 97% pure when analyzed by High Pressure Liquid Chromatography ("HPLC") at 215 nm. FAB-MS m/z 910 (HR-FAB-MS of the amino core cyclic peptide of laspartomycin: found 910.4251 $(M+H)^+$, calc. 910.4270 for $C_{38}H_{59}N_{11}O_{15}$+H). Also obtained was about 14 mg of an isomer of the amino core cyclic peptide of laspartomycin as an off white solid. FAB-MS: m/z 910$(M+H)^+$.

5.3.2 Biochemical Synthesis of the Amino Core Antibiotic and Amino Core Cyclic Peptide of Laspartomycin About 2.5 g of laspartomycin was treated with the deacylase broth under conditions similar to those described in Example 5.3.1 except where explicitly noted. About 1.0 g of laspartomycin was treated with deacylase fermentation broth at about 2.0 mg/mL for about 3.7 hrs to produce a sample enriched in the amino core antibiotic of laspartomycin. About 1.5 g of laspartomycin was treated with deacylase fermentation broth at about 5.0 mg/mL for about 20 hours. The fermentation broths were pooled and then processed as described in 5.3.1 to provide about 100 mg of the amino core antibiotic of laspartomycin and about 600 mg of the amino core cyclic peptide of laspartomycin, and an estimated 150 mg of an isomer of the amino core cyclic peptide of laspartomycin. FAB-MS of the amino core antibiotic of laspartomycin: m/z 1026$(M+H)^+$, 1048$(M+Na)^+$.

5.3.3 Synthesis of Protected Amino Core Antibiotic of Laspartomycin

Equimolar amounts of t-butoxycarbonyl-L-aspartic acid 4-O-t-butyl ester, dicyclohexylcarbodiimide, and 1-hydroxybenzotriazole in tetrahydrofuran was stirred overnight and the reaction mixture was filtered and evaporated to give a crystalline solid. The solid was then slurried in ethyl acetate, filtered and dried to provide t-butoxycarbonyl-L-aspartic acid-4-O-t-butyl ester 1-hydroxybenzotriazole ester.

A mixture of the amino core cyclic peptide of laspartomycin (15.2 mg, 0.0167 mmol) and diisopropylethlyamine (0.025 mL, 0.1437 mmol) in 0.20 mL of dimethylformamide was stirred at room temperature under nitrogen. A solution of t-butoxycarbonyl-L-aspartic acid-4-O-t-butyl ester 1-hydroxybenzotriazole ester (0.030 mL aliquots) containing 0.0496 mg (0.1218 mmol) of the activated ester in 0.20 mL was initially added and again after 0.50 hr. The progress of the reaction was followed by HPLC. Water was added to quench the reaction and the reaction mixture adsorbed on a 2.5×5.0 cm styrene-divinylbenzene resin column (ENVI™-Chrom P), and eluted with pH 7.2 phosphate buffer containing about 45% acetonitrile. Fractions containing the desired product were desalted and freeze dried to obtain 9.0 mg of the protected amino core antibiotic of laspartomycin estimated 90% pure based on HPLC. FAB-MS: m/z 1182 $(M+H)^+$, 1204 $(M+Na)^+$.

5.3.4 Synthesis of the Amino Core Antibiotic of Laspartomycin 0.35 mL of trifluoroacetic acid was added to 6.9 mg of the compound prepared above and the solution was allowed to stand at room temperature for 1.5 hr. Trifluoroacetic acid was removed and the residue was lyophilized to afford 4.8 mg of the amino core antibiotic of laspartomycin as the trifluoroacetate salt. FAB-MS: m/z 1025 $(M+H)^+$, 1047 $(M+Na)^+$, 1063 $(M+K)^+$.

5.4 Synthesis of the Hexadecylsulfonyl-L-Tryptophan Derivative of the Core Antibiotic of Laspartomycin

5.4.1 Hexadecylsulfonyl-L-Tryptophan Methyl Ester

A solution of hexadecylsulfonyl chloride (260 mg, 0.80 mmol), tryptophan methyl ester hydrochloride (254 mg, 1.0 mmol), and 0.34 mL of triethylamine (2.45 mmol) in 2.0 mL of dimethylformamide was stirred at room temperature for 4.0 hrs. The mixture was diluted with 10 mL of 1.0 N HCl and extracted with 20 mL of ethyl acetate. The ethyl acetate solution was washed with water and saturated salt solution and dried over magnesium sulfate then evaporated to give beige crystals. Yield 261 mg, FABMS: m/z 507 $(M+H)^+$.

5.4.2 Hexadecylsulfonyl-L-Tryptophan

A mixture of hexadecylsulfonyl-L-tryptophan methyl ester (260 mg 0.514 mmol), and 0.50 mL of 1.0 N NaOH in 2.0 mL of methanol and 2.0 mL of tetrahydrofuran was stirred at room temperature for several hrs. Thin layer chromatography indicated the reaction was incomplete. An additional 0.50 mL of 1.0 N NaOH was added and the mixture was stirred until reaction was complete (about 18 hrs.). The reaction was worked up as described above to afford 196 mg of product. FABMS: m/z 493 $(M+H)^+$.

5.4.3 Hexadecylsulfonyl-L-Tryptophan Derivative of the Core Antibiotic of Laspartomycin Hexadecylsulfonyl-L-Tryptophan (90 mg, 0183 mmol), hydroxybenzotriazole (28 mg, 0.183 mmol), and dicyclohexylcarbodiimide (38 mg, 0.183 mmol) was stirred for 40 minutes in 1.0 mL of dimethylformamide. A 0.30 mL aliquot of this solution was added to a solution of the amino core antibiotic of laspartomycin (94.5 mg, 0.0439 mmol) in 0.20 mL of dimethylformamide. The progress of the reaction was monitored by HPLC. At the completion of the reaction, the reaction mixture was diluted with 5 mL of methanol and 1.5M $NH_4OH$ was added to an apparent pH of about 7. The filtered sample solution was applied to a 2.5×44 cm size exclusion column (Sephadex LH-20 fine, swelled in methanol) which was eluted with methanol at about 0.8 mL/min. The product eluted in about 25 mL of eluate starting at about 105 mL. The methanol was removed from the product pool by evaporation under vacuum at or below 30° C. The solid residue was dissolved in about 12 mL of 10% acetonitrile buffered with 0.08M ammonium phosphate (aqueous pH 7.2). This solution was applied to a 2.5×5 cm styrene-divinylbenzene resin column (Supelco ENVI-Chrom P resin) and eluted with increasing concentrations of acetonitrile buffered with pH7.2 ammonium phosphate. The product eluted in about 36 mL using 48% acetonitrile eluent. Acetonitrile was removed from this fraction by evaporation under vacuum. Prior to applying this fraction to the resin column for desalting, the resin column was washed with 70% acetonitrile, then 100% acetonitrile, and finally 20% acetonitrile. The aqueous solution of the sample was applied then to the column. The column was rinsed with 28 mL of 21% acetonitrile (unbuffered) and the desalted product was stripped from the column using 67% acetonitrile. Acetonitrile was removed by evaporation under vacuum and the product was freeze dried. Yield: 14 mg white solid, $C_{69}H_{104}N_{14}O_{21}$; FABMS: m/z 1499 $(M+H)^+$, 1521 $(M+Na)^+$, 1537$(M+K)^+$.

5.5 Synthesis of the Hexadecylsulfonyl-L-Phenylalanine Derivative of the Core Antibiotic of Laspartomycin 5.5.1 Hexadecylsulfonyl-L-Phenylalanine Methyl Ester A solution of hexadecylsulfonyl chloride (617 mg, 1.87 mmol), L-phenylalanine methyl ester hydrochloride (501 mg, 2.32 mmol), and 0.60 mL of triethylamine (4.33 mmol) in 4.0 mL of dimethylformamide was stirred at room temperature for 4.0 hrs. The mixture was diluted with 20 mL of 1.0 N HCl and extracted with 20 mL of ethyl acetate. The ethyl acetate solution was washed with water and saturated salt solution and dried over magnesium sulfate then evaporated to give an oil which crystallized on standing; yield 595 mg, FABMS: m/z 468 $(M+H)^+$.

5.5.2 Hexadecylsulfonyl-L-Phenylalanine

A mixture of hexadecylsulfonyl-L-phenylalanine methyl ester (590 mg, 1.26 mmol), and 2.0 mL of 1.0 N NaOH in 4.0 mL of methanol and 2.0 mL of tetrahydrofuran was stirred at room temperature until the reaction was complete as shown by Thin Layer Chromatography. Work up was as described for the corresponding tryptophan analog in 5.4.2 above and gave the desired product; FABMS: 454 $(M+H)^+$ 476 $(M+N)^+$.

5.5.3 Hexadecylsulfonyl-L-Phenylalanine Derivative of the Core Antibiotic of Laspartomycin Hexadecylsulfonyl-L-phenylalanine (60 mg, 0.132 mmol), hydroxybenzotriazole (19 mg, 0.132 mmol), and dicyclohexylcarbodiimide (32 mg, 0.151 mmol) was stirred for 40 minutes in 0.67 mL of dimethylformamide. A 0.30 mL aliquot of this solution was added to a solution of the amino core antibiotic of laspartomycin (50 mg., 0.0488 mmol) in 0.40 mL of dimethylformamide. The progress of the reaction was monitored by HPLC and the product was isolated by chromatography in a similar fashion to that described in 5.4.3. Product was a white powder, 13 mg, $C_{67}H_{105}N_{13}O_{21}S$, FABMS: m/z 1460.5 $(M+H)^+$, 1482.4 $(M+Na)^+$, 1498.4 $(M+K)^+$.

5.6 Synthesis of the Hexadecylsulfonyl Derivative of the Core Antibiotic of Laspartomycin 5.6.1 N-Hexadecylsulfonyl Derivative of the (O-t-butyl) Core Antibiotic of Laspartomycin N-hexadecylsulfonyl-(O-t-butyl)-L-aspartic acid (189 mg, 0.395 mmol, 1-hydroxybenzotriazole (55 mg, 0.395 mmol) and dicyclohexylcarbodiimide (83 mg, 0.395 mmol) in 0.50 mL of dimethylformamide was stirred at room temperature for forty five minutes. A 0.050 mL aliquot of this solution was added to the tetrabutylammonium salt of the amino core cyclic peptide of laspartomycin in 0.2 mL of dimethylformamide and stirred at room temperature for sixty minutes. The reaction mixture was quenched by dilution with 8 mL of 25% acetonitrile, 0.12 M in ammonium phosphate (pH 7.2), aged at room temperature, then membrane filtered (Whatman GD/X). The product was isolated from the filtrate by low resolution reverse phase chromatography on a 5 g styrene-divinylbenzene resin cartridge (25×45 mm, Supelco EnviChrom-P). The sample-loaded cartridge was eluted with stepwise increasing concentrations of acetonitrile in sodium phosphate (aqueous pH 6.9); the product was eluted with 57% acetonitrile, 0.010 M in pH 6.9 buffer. The material was then desalted as described in Section 5.4.3. Yield: 4.7 mg of white solid, 69% by HPLC (215 nm area %); $C_{62}H_{104}N_{12}O_{20}S$.

5.6.2 N-Hexadecylsulfonyl Derivative of the Core Antibiotic of Laspartomycin

A solution of N-hexadecylsulfonyl-(O-t-butyl)-L-aspartyl-laspartomycin core antibiotic (4.7 mg) in 0.50 mL of 95% trifluoroacetic acid was stirred at room temperature for 30 min. Trifluoroacetic acid was removed with a stream of dry nitrogen and the residue was triturated with t-butylmethyl ether and centrifuged. Excess ether was removed and the resulting solid was dissolved in 1.5 mL of water by adding 1 drop of 3% ammonium hydroxide, then freeze dried. Yield: 2.5 mg of solid, 63% by HPLC (215 nm area %); $C_{58}H_{96}N_{12}O_{20}S$; FABMS m/z 1313 $(M+H)^+$, 1335 $(M+Na)^+$. Calculated for $C_{58}H_{96}N_{12}O_{20}S+H$, 1313.

5.7 Synthesis of the Hexadecylsulfonyl-L-Phenylalanine Derivative of the Core Antibiotic of Aspartocin 5.7.1 N-Hexadecylsulfonyl-L-Phenylalanine Derivative of the Core Antibiotic of FMOC-Aspartocin A mixture of N-hexadecylsulfonyl-L-phenylalanine (100 mg, 0.220 mmol), 1-hydroxybenzotriazole (35.5 mg, 0.232 mmol), and dicyclohexylcarbodiimide (45 mg, 0.218 mmol) in 0.95 mL of dimethylformamide was stirred at room temperature for 45 minutes. A 0.30 mL aliquot of this solution was added to a solution of the FMOC derivative of the amino core antibiotic of aspartocin (80 mg, obtained from FMOC-Aspartocin as described in section 5.2.3) in 0.50 mL dimethylformamide. Additional aliquots of 0.30 mL and 0.15 mL of the activated ester were added after 35 and 70 minutes. The reaction mixture was quenched by addition of 5 mL of methanol and the pH was adjusted to pH 7 (using pH paper) by addition of 0.55 mL of 1.5 M ammonium hydroxide. The quenched solution was membrane filtered (Whatman GD/X) and the filtrate was applied to a Sephadex LH-20 column (25×420 mm) equilibrated in methanol. The sample was eluted with methanol at about 0.8 mL/min and the methanol was removed under vacuum. The product was further purified by preparative HPLC (Waters Delta-Pak C 18 column, 25×110 mm) using 53% isopropanol and 0.03 M in ammonium acetate (aqueous pH 5.4) at a flow rate of 10 mL/min at room temperature. Isopropanol was removed under vacuum and the pH of the turbid aqueous solution was adjusted to pH 6 with dilute ammonium hydroxide. The product was desalted and freeze dried as previously described above. Yield: 16 mg of a white solid, 66% by HPLC (215 nm area %); $C_{85}H_{120}N_{14}O_{24}S$; FABMS m/z 1776 $(M+Na)^+$, 1791$(M+K)^+$. Calculated for $C_{85}H_{120}N_{14}O_{24}S+Na$, 1776).

5.7.2 N-Hexadecylsulfonyl-L-Phenylalanine Derivative of the Core Antibiotic of FMOC-Aspartocin A solution of 10.4 mg of the product of Section 5.7.1 in 1.0 mL of 2/1 DMSO-methanol and 0.020 mL of piperdine was stirred for 90 minutes at room temperature, diluted with 10 mL of 20% acetonitrile in 0.040 M in ammonium phosphate (pH7.2), then membrane filtered (Whatman GD/X). The filtrate was applied to a conditioned 0.5 g resin cartridge (Supelco EnviChrom-P) which was then rinsed with salt-free 20% acetonitrile (6 mL). The product was stripped from the cartridge with 4 mL of 60% acetonitrile, acetonitrile was removed under vacuum and the product freeze dried from aqueous solution. Yield: 7 mg of a white solid, 74% by HPLC (215 nm area %); $C_{70}H_{110}N_{14}O_{22}S$; FABMS m/z 1533(M+H)$^+$, 1555(M+Na)$^+$, 1571(M+K)$^+$. Calculated for $C_{70}H_{110}N_{14}O_{22}S+Na$, 1532, (instrument error at this mass range is ±0.5 mass units).

5.8 Resistance of Sulfonamide Derivatives to the Deacylase Enzyme

One milligram of the hexadecylsulfonyl-L-tryptophan derivative of the core antibiotic of laspartomycin (see Section 5.4 for preparation) was added to 2 mL of deacylase broth (prepared as described in Section 5.1) and a zero time sample (0.5 mL) was removed and stored by freezing. The reaction mixture was placed on a shaker at 200 rpm and 84° C. for 16 hours. The zero and 16 hour samples were then studied by HPLC and by agar well zone diffusion assay using *Staphylococuss aureus* as a test organism. The same conditions were used to compare laspartomycin to enzyme deactivation. The table below shows the results which indicate complete deactivation of laspartomycin by the enzyme preparation while the hexadecylsulfonyl-L-tryptophan derivative of the core antibiotic of laspartomycin was degraded at a much slower rate. Under the same conditions Antibiotic A21978C and Aspartocin were completely deactivated within two hours and 16 hours, respectively.

| Compound | Bioassay zone dia.[a] | | HPLC Peak Area[b] | |
|---|---|---|---|---|
| | Zero time | 16 hours | zero time | 16 hours |
| Laspartomycin | 15.5 mm | no zone | 100% | 0% |
| Hexadecylsulfonyl-L-tryptophan derivative of the core antibiotic of laspartomycin | 13.7 mm | 12.8 mm | 100% | 53% |

[a]9 mm well in agar seeded with *Staphylococuss aureus* wells filled with 100 μl of sample and incubated for 16 hrs. at 28° C.
[b]HPLC with reverse phase column, Phenomenex, ® Prodigy ™ 5 μ ODS (2), 250 × 4.60 mm, using gradient elution; gradient was 0.05 molar phosphate buffer, pH 7.2, with 10% CH$_3$CN going to 75% CH$_3$CN in water in 8 minutes. Retention times were 9.62(main component) and 13.13 minutes for laspartomycin and the hexadecylsulfonyl-L-tryptophan derivative of the core antibiotic of laspartomycin, respectively.

5.9 MIC Data for Antimicrobial Sulfonamides

MIC values were determined by microliter serial dilution using *Staphlococcus aureus* strain Smith as the assay organism, which was grown in Mueller-Hinton broth with and without CaCl$_2$.

| | MIC(mg/mL) | |
|---|---|---|
| Name | w/o CaCl$_2$ | w CaCl$_2$ (4 mm) |
| Aspartocin | 2 | 1 |
| Laspartomycin | 16 | 2 |
| 52 | 8–16 | 4 |
| 54 | >64 | >64 |

| | MIC(mg/mL) | |
|---|---|---|
| Name | w/o CaCl$_2$ | w CaCl$_2$ (4 mm) |
| 56 | 8 | 4 |
| 58 | 32 | 1 |
| 60 | >64 | >64 |
| 62 | 4 | 4 |

While the invention has been described in some detail to facilitate understanding, it will be apparent that certain changes and modifications may be practiced within the scope of the appended claims. For example, lipophilic side chains could be used in practicing the methods of the current invention. Therefore, the above described embodiments should be considered illustrative and not restrictive and the instant invention is not limited to the details given herein but may be modified within the scope of the appended claims.

All publications cited herein are incorporated by reference in their entireties.

We claim:

1. An antimicrobial sulfonamide derivative, or a salt or a hydrate thereof, comprising:

a core cyclic peptide or core antibiotic of an acidic lipopeptide antibiotic; and a lipophilic moiety, wherein said lipophilic moiety is covalently attached to the core cyclic peptide or core antibiotic via a linking chain which includes a sulfonamide linkage and wherein said core cyclic peptide or core antibiotic is not of laspartomycin.

2. The antimicrobial sulfonamide derivative, salt or hydrate of claim 1 in which the linking chain is a sulfonamide linkage.

3. The antimicrobial sulfonamide derivative, salt or hydrate of claim 1 in which the linking chain is a linker that links the core cyclic peptide or core antibiotic to the lipophilic moiety.

4. The antimicrobial sulfonamide derivative, salt or hydrate of claim 1 which is a compound according to structural Formula (I):

$$Y—X—N(R^4)(-L—X—N(R^1))_m—R \quad (I)$$

wherein:

Y is a lipophilic moiety;

each X is independently selected from the group consisting of —CO—SO$_2$—, —CS—, —PO—, —OP(O)—, —OC(O)—, —NHCO and —N(R$^1$)CO— with the proviso that at least one X is —SO$_2$—;

M is 0 or 1;

L is a linker;

N is nitrogen;

R$^1$ and R$^4$ are each independently selected from the group consisting of hydrogen, (C$_1$–C$_{25}$) alkyl optionally substituted with one or more of the same or different R$^2$ groups, (C$_1$–C$_{25}$) heteroalkyl optionally substituted with one or more of the same or different R$^2$ groups, (C$_5$–C$_{30}$) aryl optionally substituted with one or more of the same or different R$^2$ groups, (C$_5$–C$_{30}$) arylaryl optionally substituted with one or more of the same or different R$^2$ groups, (C$_5$–C$_{30}$) biaryl optionally substituted with one or more of the same or different R$^2$ groups, five to thirty membered heteroaryl optionally substituted with one or more of the same or different $R^2$ groups, $(C_6-C_{30})$ arylalkyl optionally substituted with one or more of the same or different $R^2$ groups and six to thirty membered heteroarylalkyl optionally substituted with one or more of the same or different $R^2$ groups;

each $R^2$ is independently selected from the group consisting of —$OR^3$, —$SR^3$, —$NR^3R^3$, —CN, —$NO_2$, —$N_3$, —C(O)$OR^3$, —C(O)$NR^3R^3$, —C(S)$NR^3R^3$, —C($NR^3$)$NR^3R^3$, —CHO, —$R^3$CO, —$SO_2R^3$, —$SOR^3$, —PO($OR^3$)$_2$, —PO($OR^3$), —$CO_2H$, —$SO_3H$, —$PO_3H$, halogen and trihalomethyl;

each $R^3$ is independently selected from the group consisting of hydrogen, $(C_1-C_6)$ alkyl, $(C_5-C_{10})$ aryl, five to sixteen membered heteroaryl, $(C_6-C_{16})$ arylalkyl and six to sixteen membered heteroarylalkyl; and R is a core cyclic peptide or core antibiotic of an acidic lipopeptide antibiotic, wherein said core cyclic peptide or core antibiotic is not of laspartomycin.

5. The antimicrobial sulfonamide derivative of claim 4 in which R is the core cyclic peptide of zaomycin, crystallomycin, aspartocin, amphomycin, glumamycin, brevistin, cerexin A, cerexin B, Antibiotic A-30912, Antibiotic A-1437, Antibiotic A-54145, Antibiotic A-21978C or tsushimycin.

6. The antimicrobial sulfonamide derivative of claim 4 in which R is the core antibiotic of zaomycin, crystallomycin, aspartocin, amphomycin, glumamycin, brevistin, cerexin A, cerexin B, Antibiotic A-30912, Antibiotic A-1437, Antibiotic A-54145, Antibiotic A-21978C or tsushimycin.

7. The antimicrobial sulfonamide derivative of claim 4 in which R is the core cyclic peptide of aspartocin, Antibiotic A*-30912, Antibiotic A-1437, Antibiotic A-54145 or Antibiotic A-21978C.

8. The antimicrobial sulfonamide derivative of claim 4 in which R is the core antibiotic of aspartocin, Antibiotic A-30912, Antibiotic A-1437, Antibiotic A54145 or Antibiotic A-21978C.

9. The antimicrobial sulfonamide derivative of claim 4 in which R is the core cyclic peptide of aspartocin.

10. The antimicrobial sulfonamide derivative of claim 4 in which R is the core antibiotic of aspartocin.

11. The antimicrobial sulfonamide derivative of claim 4 in which m is 1.

12. The antimicrobial sulfonamide derivative of claim 4 in which $R^1$ and $R^4$ are hydrogen.

13. The antimicrobial sulfonamide derivative of claim 4 in which L is selected from the group consisting of:

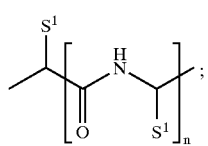
(L1)

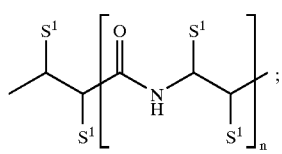
(L2)

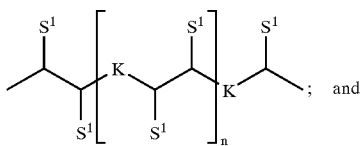
(L3)

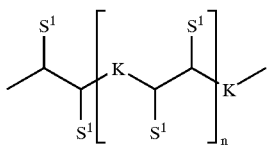
(L4)

or a pharmaceutically acceptable salt or hydrate thereof, wherein:

n is 0, 1, 2 or 3;

each $S^1$ is independently selected from the group consisting of hydrogen, $(C_1-C_{10})$ alkyl optionally substituted with one or more of the same or different $R^5$ groups, $(C_1-C_{10})$ heteroalkyl optionally substituted with one or more of the same or different $R^5$ groups, $(C_5-C_{10})$ aryl optionally substituted with one or more of the same or different $R^5$ groups, $(C_5-C_{15})$ arylaryl optionally substituted with one or more of the same or different $R^5$ groups, $(C_5-C_{15})$ biaryl optionally substituted with one or more of the same or different $R^5$ groups, five to ten membered heteroaryl optionally substituted with one or more of the same or different $R^5$ groups, $(C_6-C_{16})$ arylalkyl optionally substituted with one or more of the same or different $R^5$ groups and six to sixteen membered heteroarylalkyl optionally substituted with one or more of the same or different $R^5$ groups;

each $R^5$ is independently selected from the group consisting of —$OR^6$, —$SR^6$, —$NR^6R^6$, —CN, —$NO_2$, —$N_3$, —C(O)$OR^6$, —C(O)$NR^6R^6$, —C(S)$NR^6R^6$, —C($NR^6$)$NR^6R^6$, —CHO, —$R^6$CO, —$SO_2R^6$, —$SOR^6$, —PO($OR^6$)$_2$, —PO($OR^6$), —$CO_2H$, —$SO_3H$, —$PO_3H$, halogen and trihalomethyl;

each $R^6$ is independently selected from the group consisting of hydrogen, $(C_1-C_6)$ alkyl, $(C_5-C_{10})$ aryl, five to sixteen membered heteroaryl, $(C_6-C_{16})$ arylalkyl and six to sixteen membered heteroarylalkyl; and each K is independently selected from the group consisting of oxygen, nitrogen and sulfur.

14. The antimicrobial sulfonamide of claim 13 in which each $S^1$ is independently a side-chain of a genetically encoded α-amino acid.

15. The antimicrobial sulfonamide of claim 13 in which L is:

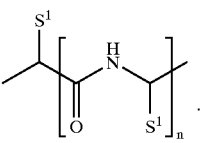

16. The antimicrobial sulfonamide derivative of claim 15 in which each $S^1$ is independently a side-chain of a genetically encoded α-amino acid.

17. The antimicrobial sulfonamide derivative of claim 15 in which n is 0.

18. The antimicrobial sulfonamide derivative of claim 17 in which $S^1$ is hydrogen, Y is decan-yl and R is the core cyclic peptide of aspartocin.

19. The antimicrobial sulfonamide derivative of claim 17 in which $S^1$ is —CH$_2$—CO$_2$H, —CH$_2$—CH$_2$—CO$_2$H, —C(OH)H—CONH$_2$, —CH$_2$—CONH$_2$ or —CH$_2$-CH$_2$—CONH$_2$ or a salt or hydrate thereof.

20. The antimicrobial sulfonamide derivative of claim 17 in which $S^1$ is —CH$_2$-indol-2-yl or —CH$_2$-phenyl.

21. The antimicrobial sulfonamide derivative of claim 13 in which L is:

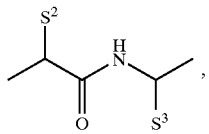

wherein $S^2$ and $S^3$ are each independently a side chain of a genetically encoded α-amino acid.

22. The antimicrobial sulfonamide derivative of claim 21 in which $S^2$ is hydrogen, —CH$_2$-indol-2-yl, —CH$_2$—CONH$_2$ or —CH$_2$—CH$_2$—CONH$_2$ and $S^3$ is —CH$_2$—CO$_2$H, —CH$_2$—CH$_2$—CO$_2$H or a salt or hydrate thereof.

23. The antimicrobial sulfonamide derivative of claim 21 in which $S^2$ is —CH$_2$—CO$_2$H, —CH$_2$—CH$_2$—CO$_2$H or a salt or hydrate thereof and $S^3$ is —C(OH)H—CONH$_2$.

24. The antimicrobial sulfonamide derivative of claim 13 in which L is:

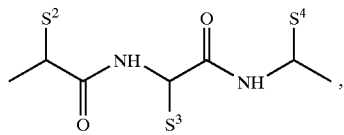

wherein $S^2$, $S^3$, and $S^4$ are each independently a side chain of a genetically encoded α-amino acid.

25. The antimicrobial sulfonamide derivative of claim 24 in which $S^2$ is —CH$_2$-indol-2-yl, $S^3$ is —CH$_2$—CONH$_2$ or —CH$_2$—CH$_2$—CONH$_2$ and $S^4$ is —CH$_2$—CO$_2$H, —CH$_2$—CH$_2$—CO$_2$H or a salt or hydrate thereof.

26. The antimicrobial sulfonamide derivative of claim 24 in which $S^2$ is —CH$_2$-indol-2-yl, $S^3$ is —CH$_2$—CO$_2$H, CH$_2$—CH$_2$—CO$_2$H or a salt or hydrate thereof and $S^4$ is —CH$_2$—CONH$_2$, —CH$_2$—CH$_2$—CONH$_2$ or —C(OH)H—CONH$_2$.

27. The antimicrobial sulfonamide derivative of claim 4 in which m is 0.

28. The antimicrobial sulfonamide derivative of claim 27 in which $R^4$ is hydrogen.

29. The antimicrobial sulfonamide derivative of claim 27 which R is the core antibiotic of aspartocin.

30. The antimicrobial sulfonamide derivative of claim 27 in which R is the core cyclic peptide of aspartocin.

31. A pharmaceutical composition comprising an antimicrobial sulfonamide derivative according to any one of claims 1 to 5 and a pharmaceutically acceptable adjuvant, excipient, carrier or diluent.

32. A method for treating or preventing a microbial infection, said method comprising the step of administering to a subject a therapeutically effective amount of a pharmaceutical composition according to claim 31.

33. A method of inhibiting microbial growth, said method comprising the step of administering to a microbe an antimicrobially effective amount of a pharmaceutical composition according to claim 31.

34. A method for making an antimicrobial sulfonamide derivative comprising sulfonylating a core antibiotic or core cyclic peptide with a lipophilic sulfonyl derivative, thereby providing an antimicrobial sulfonamide derivative.

35. The method of claim 34 in which the lipophilic sulfonyl derivative is an activated lipophilic sulfonyl ester or a lipophilic sulfonyl halide.

36. The method of claim 35 in which the activated lipophilic sulfonyl ester is a lipophilic hydroxybenzotriazole ester.

37. The method of claim 35 in which the lipophilic sulfonyl halide is a lipophilic sulfonyl chloride.

38. A method for making an antimicrobial sulfonamide derivative comprising:

sulfonylating a linker with a lipophilic sulfonyl compound, thereby providing a lipophilic sulfonamide linker; and covalently attaching the lipophilic sulfonamide linker to a core antibiotic or core cyclic peptide wherein said core cyclic peptide or core antibiotic is of an acidic lipopeptide antibiotic, thereby yielding an antimicrobial sulfonamide derivative.

39. A method for making an antimicrobial sulfonamide derivative comprising:

covalently attaching a linker to a core antibiotic or core cyclic peptide, thereby providing an linker core antibiotic or linker core cyclic peptide; and sulfonylating the linker core antibiotic or linker core cyclic peptide with a lipophilic sulfonyl derivative, thereby yielding an antimicrobial sulfonamide derivative.

40. A method for treating or preventing a microbial infection, said method comprising the step of administering to a subject a therapeutically effective amount of an antimicrobial sulfonamide derivative according to any one of claims 1 to 5.

41. The method of claim 40 in which the core cyclic peptide is aspartocin.

42. The method of claim 40 in which the core antibiotic is aspartocin.

43. A method of inhibiting microbial growth, said method comprising the step of administering to a microbe an antimicrobially effective amount of an antimicrobial sulfonamide derivative according to any one of claims 1 to 5.

44. The method of claim 43 in which the core cyclic peptide is aspartocin.

45. The method of claim 43 in which the core antibiotic is aspartocin.

* * * * *